(12) United States Patent
Ball et al.

(10) Patent No.: US 7,977,320 B2
(45) Date of Patent: Jul. 12, 2011

(54) METHOD OF INCREASING EFFICACY OF TUMOR CELL KILLING USING COMBINATIONS OF ANTI-NEOPLASTIC AGENTS

(75) Inventors: Edward D. Ball, San Diego, CA (US); Larissa Balaian, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1015 days.

(21) Appl. No.: 11/718,127

(22) PCT Filed: Oct. 28, 2005

(86) PCT No.: PCT/US2005/038904
§ 371 (c)(1),
(2), (4) Date: Jul. 30, 2007

(87) PCT Pub. No.: WO2006/050075
PCT Pub. Date: May 11, 2006

(65) Prior Publication Data
US 2008/0069818 A1     Mar. 20, 2008

Related U.S. Application Data

(60) Provisional application No. 60/623,060, filed on Oct. 29, 2004.

(51) Int. Cl.
*A01N 43/04* (2006.01)
*A61K 31/70* (2006.01)
(52) U.S. Cl. ................. 514/43; 514/42; 514/49; 514/45
(58) Field of Classification Search ........................ None
See application file for complete search history.

(56) References Cited

U.S. PATENT DOCUMENTS

| | | | |
|---|---|---|---|
| 4,671,477 A * | 6/1987 | Cullen | 248/122.1 |
| 6,007,814 A | 12/1999 | Scheinberg | |
| 6,759,045 B2 | 7/2004 | Goldenberg et al. | |
| 2004/0152632 A1 | 8/2004 | Feingold | |

FOREIGN PATENT DOCUMENTS

WO    WO 2004/043461      5/2004

* cited by examiner

*Primary Examiner* — Patrick Lewis
(74) *Attorney, Agent, or Firm* — Sutherland Asbill & Brennan LLP

(57) ABSTRACT

The present invention provides compositions and methods for increasing the amount of active Syk protein kinase and or SHP-1 protein phosphatase in a cell. The compositions and methods are useful for increasing the efficacy of anti-neoplastic agents, such as those that target the CD33 protein, and which are used to treat leukemia. The invention thus provides for treatment of cancers, including leukemias. The invention also provides screening assays for anti-neoplastic agents in vitro. Methods of screening patients for responsiveness to anti-CD33 treatments are also provided.

21 Claims, 7 Drawing Sheets

METHOD OF INCREASING EFFICACY OF TUMOR CELL KILLING USING COMBINATIONS OF ANTI-NEOPLASTIC AGENTS

CROSS-REFERENCE TO RELATED APPLICATIONS

This application claims the benefit of and relies on the filing date of U.S. Provisional Patent Application No. 60/623,060, filed 29 Oct. 2004, and international application PCT/US2005/038904, filed 28 Oct. 2005, the entire disclosures of both of which are hereby incorporated herein by reference.

GOVERNMENT INTERESTS

This invention was made with U.S. Government support under Grant No. CA31888 from the National Institutes of Health. The Government has certain rights in this invention.

BACKGROUND OF THE INVENTION

1. Field of the Invention

The present invention relates to the field of treatment of neoplastic diseases and uncontrolled cell growth. More specifically, it relates to compositions and methods for treating tumors or cancers with combinations of a substance that activates a signalling pathway involving SHP-1, Syk, or both, and an anti-neoplastic agent that binds to a cell surface protein, such as a substance that binds CD33 molecules on the surface of neoplastic cells.

2. Description of Related Art

Neoplastic diseases, or cancers, are a leading cause of death in the world. Neoplastic diseases have been classified using various different schemes. One useful scheme differentiates the diseases based on the types of cells involved: solid tumors (which originate from cells of any tissue other than blood, bone marrow, or the lymphatic system) and non-solid tumors (which include cancers of the blood, bone marrow, and lymphatic system, such as leukemias and lymphomas).

Solid tumors can be of numerous types, each derived from a cell of a tissue of the body. On the other hand, non-solid tumors are of a limited type, due to the limited number of cell types in blood, bone marrow, and the lymphatic system. Leukemias are likely the most devastating type of non-solid tumor because they strike young children at a high rate and are particularly difficult to treat. Leukemias can be divided into two types: acute and chronic. Acute leukemias are leukemias of undifferentiated cells, whereas chronic leukemias contain mature, differentiated cells. Acute leukemias can be of two types: 1) lymphoblastic (ALL) and 2) non-lymphoblastic (ANLL), which is also known as acute myeloblastic leukemia or acute myeloid leukemia (AML). Chronic leukemias can also be of two types: 1) lymphocytic (CLL) and 2) myelocytic or myeloid (CML).

Numerous ways of treating neoplastic diseases have been developed over the years. The treatment of choice is typically surgery to remove the tumor because this type of treatment shows a high rate of success and is minimally damaging to unaffected cells of the body. However, many cancers do not lend themselves to surgery, and thus require alternative methods of treatment. Generally, non-surgical treatments include administering to the patient substances that are cytotoxic, and thus cause cell death (i.e., administering chemotherapeutic agents), exposure to cell-killing amounts of radiation, or both. The crudest treatments with cytotoxic agents use substances that do not differentiate between normal and neoplastic cells. Thus, while cancer cells are killed by the treatment, normal, healthy cells are killed as well. As the field of cancer treatment has evolved, the substances used for treatment have become more selective, being targeted only to growing cells or cells with proteins on their surfaces that are specific for cancer cells.

Because non-solid cancers are not confined to any single area of the body, treatment with surgery or radiation is not practical as the sole method of treatment. Likewise, because systemic killing of all cells of the body is undesirable, cytotoxic agents to be used in treating non-solid tumors should specifically target the cancer cells while avoiding non-cancer cells. Antibodies that are specific for cell-surface proteins that are typically expressed on cancer cells, but not normal cells, are particularly well suited for treatment of non-solid tumors. Indeed, it has been found that antibodies to the surface protein CD33, which is expressed on most myeloid leukemia cells, can be effective in treating this type of leukemia. Antibodies against CD33 are also attractive as therapeutic agents because it has been reported that the CD33 molecule is not expressed on the surface of normal hematopoietic stem cells, thus allowing for killing of cancerous cells while sparing the cells needed for repopulation of the bone marrow and the blood system.

To further improve the killing effectiveness of antibodies for non-solid tumor cells, various cytotoxic agents have been conjugated to antibodies that specifically bind the non-solid tumor cells. Such immunoconjugates or immunotoxins have proven to be effective in treating non-solid tumors. For example, a monoclonal antibody-chalicheamicin immunoconjugate (Mylotarg®, Wyeth, Madison, N.J.) that specifically binds CD33 has been approved by the FDA for first recurrence of AML. Other immunoconjugates, specific for CD33 or other cell-surface proteins on leukemia cells, have also been disclosed as effective.

For example, U.S. Pat. No. 6,759,045 to Goldenberg et al. discloses that naked anti-NCA90 antibodies or anti-NCA33 immunotoxins or immunoconjugates can be used to treat CML and AML. This patent discloses that the antibodies can be used alone or in combination with other substances, such as agents that induce expression of target molecules (e.g., expression of NCA-90). The patent also discloses that the antibodies can be used in conjunction with chemotherapeutic agents, such as daunorubicin, cytarabine, 6-thioguanine, etoposide, mitoxantrone, diaziquone, idarubicin, and others.

In addition, U.S. Pat. No. 6,007,814 to Scheinberg discloses mouse antibodies (M195) and fragments that are specific for CD33. It also discloses that such antibodies can be used to treat and diagnose leukemia in human patients. The antibodies can be used alone or in the form of immunoconjugates with toxins (immunotoxins). The patent discloses that this mouse antibody was administered to ten human patients, and that administration led to delivery of the M195 antibody to leukemia cells, but additionally resulted in an immune reaction against the M195 antibody (human anti-murine antibody response; HAMA). The patent further discloses that the M195 antibody was used in trials on patients who had previously failed to respond to certain chemotherapeutic agents or combinations of chemotherapeutic agents, such as idarubicin (IDA), cytosine arabinoside (Ara-C), mitoxantrone; hydroxyurea, daunomycin, and VP-16. However, due largely to the HAMA reaction, this antibody and human therapies involving this antibody have not been found to be clinically useful.

A recent study by the inventors showed a correlation between the presence of the protein kinase Syk in AML cells and anti-CD33 antibody growth inhibition of AML cells. (Balaian, L. et al., 2003.) The study showed that about one-half of AML cells are susceptible to growth inhibition and apoptosis-mediated cell death as a result of CD33 ligation by anti-CD33 antibodies, while about one-half are unresponsive to such anti-CD33 antibody treatment. That study also presented data consistent with the proposition that the Syk protein kinase is a tumor suppressor, and that lack of the protein itself, or perhaps functional Syk protein, is associated with resistance to inhibition and apoptosis-mediated cell death resulting from CD33 ligation. The authors postulated that determination of Syk expression level and/or functional activity of a patient prior to therapy could be useful in prognosing response of the patient to anti-CD33 mAb treatment. They also speculate that modulation of Syk expression could be a mechanism for increasing the efficacy of anti-CD33 mAb treatment.

MYLOTARG® (gemtuzumab ozogamicin; GO) is an anti-CD33 immunotoxin formed from the chemical conjugation of a recombinant humanized monoclonal mouse antibody (hP67.6) and calicheamicin, a potent bacterial toxin. In the immunotoxin, two to three calicheamicin molecules are chemically conjugated with the CD33 monoclonal antibody. Mylotarg was the first immunotoxin to be approved by FDA, and the first drug specifically approved to treat relapsed acute myelogenic leukemia (AML). Mylotarg is thought to be particularly well suited for treatment of AML because CD33 is expressed by leukemic blast cells and immature cells of myelomonocytic origin and other bone marrow hematopoietic cells, but not on normal pluripotent progenitor (stem) cells.

Although numerous studies have shown the effectiveness or potential effectiveness of antibodies and immunoconjugates as treatment agents for neoplasias, including non-solid tumors, because a certain portion of cells of a given neoplasia typically do not express a selected target protein on their cell surfaces, or are otherwise refractory to treatment with such agents, treatments using antibodies or immunoconjugates are not 100% effective. Thus, there exists a need in the art to improve the killing efficacy of antibodies and immunoconjugates.

SUMMARY OF THE INVENTION

The present invention addresses the need in the art by providing a method of improving the killing efficacy of treatments for neoplasias using CD33-binding agents. The present invention achieves the improvement by treating a patient with a substance that increases the amount of active Syk protein and/or SHP-1 protein in the target neoplastic cells before or during treatment with an agent that specifically binds the CD33 protein. It has been found that certain neoplastic cells expressing relatively high levels of active Syk protein and/or active SHP-1 protein are more susceptible to killing by agents that target CD33 than cells not expressing the active forms of these proteins. This discovery has lead to the realization that treatment of tumor cells with agents that increase the expression of Syk and/or SHP-1, or that increase the amount of active Syk and/or SHP-1 in a neoplastic cell can improve the efficacy of treatments that target protein activation cascades in which these proteins are members, such as those involving ligation of the cell-surface protein CD33.

The present invention also addresses needs in the art by providing a method of determining or identifying patients who are, or have a high likelihood of being, refractory to anti-neoplastic treatments based on therapeutic agents that bind to the CD33 protein. Because the methods permit one to determine these likely non-responders, it allows practitioners to modify a typical chemotherapeutic regimen that includes administration of a CD33 binding agent, such as an anti-CD33 antibody, to further include treatment with one or more substances that increase the amount or activity of the Syk protein and/or SEP-1 protein. This aspect of the invention can provide the benefit not only of reducing the number of cancer patients who are subjected to ineffective chemotherapeutic treatment regimens (e.g., those who would be non-responsive to treatments comprising anti-CD33 antibody only), but can also provide the benefit of providing an effective chemotherapeutic regimen in patients who were or would have been non-responsive to other therapeutic regimens.

In its most basic form, the present invention is based, at least in part, on the discovery that cells that are refractory to anti-neoplastic agents that function by initiating a cell killing process by binding to the CD33 cell-surface protein (e.g., anti-CD33 antibodies) can be rendered responsive to those agents by pre-treatment or co-treatment with substances that increase the amount or activity of proteins involved in a signalling pathway involving Syk, SHP-1, or both of these. Stated another way, the invention is based, at least in part, on the discovery that amounts and activity levels of Syk, SHP-1, or both of these can be used in prognosis of a treatment regimen that is based on use of anti-neoplastic agents that function by initiating a cell killing process by binding to CD33. Through use of the present invention, effective treatment regimens can be instituted for patients who were previously refractive to certain treatments, ineffective treatment regimens can be avoided in certain sub-populations of patients suffering from neoplastic diseases, and an overall improvement in anti-neoplastic therapies can be achieved. Various aspects of the invention can be used alone or in combination with other aspects to achieve the benefits described herein.

One aspect of the invention provides a method of increasing the amount of functionally active Syk protein kinase in a cell by exposing the cell to a suitable substance for a sufficient amount of time to achieve the desired effect or level of effect. The substance can act at the level of transcription, for example by increasing the amount of expression of the syk gene. Alternatively, it can act at the level of translation by stabilizing the syk mRNA or otherwise increasing the amount of Syk protein produced from mRNA. In addition, it can act post-translationally, by, for example, stabilizing the Syk protein kinase through post-translational modifications of the Syk protein (e.g., phosphorylation or dephosphorylation at one or more sites on the protein), or by aiding in proper folding of the Syk protein. The method can be practiced in vivo or in vitro, to provide a variety of useful assays, including, but not limited to, research methods, diagnostic and clinical methods, and therapeutic methods.

In view of the medical significance of this aspect of the invention, one aspect of the invention is a method of increasing the presence of functional Syk protein in cells of a patient suffering from a neoplasia, such as a cancer. In general, the method comprises administering to a patient suffering from at least one type of neoplasia, such as one suffering from a non-solid tumor, an amount of at least one substance capable of increasing the amount of active Syk protein in at least one neoplastic cell of the patient. The method results in improving the responsiveness of the patient's neoplastic cells to cell-killing agents that can be administered in addition to the active Syk-increasing substance, such agents being administered before, during, and/or after administration of the active Syk-increasing substance.

Another aspect of the invention provides a method of increasing the amount of functionally active SHP-1 protein kinase in a cell by exposing the cell to a suitable substance for a sufficient amount of time to achieve the desired effect or level of effect. The substance can act at the level of transcription, for example by increasing the amount of expression of the gene encoding SHP-1. Alternatively, it can act at the level of translation by stabilizing the SHP-1 mRNA or otherwise increasing the amount of SHP-1 protein produced from mRNA. In addition, it can act post-translationally, by, for example, stabilizing the SHP-1 protein kinase through post-translational modifications of the SHP-1 protein (e.g., phosphorylation or dephosphorylation at one or more sites on the protein), or by aiding in proper folding of the SHP-1 protein. The method can be practiced in vivo or in vitro, to provide a variety of useful assays, including, but not limited to, research methods, diagnostic and clinical methods, and therapeutic methods.

In view of the medical significance of this aspect of the invention, one aspect of the invention is a method of increasing the presence of functional SHP-1 protein in cells of a patient suffering from a neoplasia, such as a cancer. In general, the method comprises administering to a patient suffering from at least one type of neoplasia, such as one suffering from a non-solid tumor, an amount of at least one substance capable of increasing the amount of active SHP-1 protein in at least one neoplastic cell of the patient. The method results in improving the responsiveness of the patient's neoplastic cells to cell-killing agents that can be administered in addition to the active SHP-1-increasing substance, such agents being administered before, during, and/or after administration of the active SHP-1-increasing substance. In certain embodiments, the method of increasing the presence of functional SHP-1 protein in cells also comprises increasing the presence of functional Syk protein in cells.

The method of increasing active Syk and/or SHP-1 can further comprise administering at least one other substance that initiates a biological response resulting in death of a cell, where the biological response involves active Syk and/or SHP-1 protein at one or more steps. For example, the other substance can be one that binds to the cell surface protein CD33.

Accordingly, the present invention provides a method of treating a patient suffering from a neoplasia, including those suffering from a tumor or a cancer. The method comprises administering at least one substance capable of increasing the amount of active Syk, SHP-1, or both of these protein in at least one cell of the tumor or cancer. The method can further comprise administering at least one other substance that initiates a biological response resulting in death of a cell by way of binding to a CD33 molecule, where the biological response involves active Syk and/or SHP-1 protein at one or more steps. The method is particularly advantageously practiced on patients who have previously failed to respond to treatments based on administration of the substance alone.

The present invention thus provides for the use of at least one substance capable of increasing the amount of active Syk and/or SHP-1 protein in at least one cell of a neoplasia to make a pharmaceutical composition, and the use of the substance(s) in the treatment of at least one neoplasia. The invention further provides for the use of such substance(s) alone or in combination with at least one other substance that initiates a biological response resulting in death of a cell, where the biological response involves active Syk and/or SHP-1 protein at one or more steps and involves binding to at least one CD33 molecule. Such a use can be for the production of a pharmaceutical composition or combination of compositions, or can be for the use in treating at least one neoplasia.

In another aspect, the invention provides methods of identifying patients who are or have a high likelihood of being refractory (non-responsive) to anti-neoplasia treatments that are based on binding of a cell-killing agent to the cell-surface protein CD33. The method comprises obtaining a neoplastic cell from the neoplasia that is the target of the cell-killing agent that binds CD33, and determining the presence and activity level of the Syk and/or SHP-1 protein from that cell. The presence of active Syk and/or SHP-1 is indicative of the likelihood of successful treatment of the neoplasia with the cell-killing agent, where higher levels of active Syk and/or SHP-1 are correlated with higher likelihood of successful treatment. In embodiments, the activity levels of these proteins can be inferred by their phosphorylation state, or can be determined by amounts of the proteins, individually or together, as members of a complex of proteins involving at least Syk and SHP-1. These measurements may be compared, if desired, to the amounts in normal non-cancerous cells and/or responsive cancerous cells that have been activated by the CD-33 binding agent, or such cells that have not been activated by the CD-33 binding agent, in order to determine a base-line level of activation or non-activation against which to compare the test cells.

In yet another aspect, the invention provides methods of prognosing the likelihood of a patient being refractory to anti-neoplasia treatments that are based on binding of a cell-killing agent to a CD33 cell-surface protein. The method comprises obtaining at least one neoplastic cell from the neoplasia that is the target of the cell-killing agent, and determining the presence and activity level of the Syk and/or SHP-1 protein from that cell. The presence of active Syk and/or SHP-1 (e.g., phosphorylated proteins or proteins in a complex with each other) is indicative of the likelihood of successful treatment of the neoplasia with the cell-killing agent, where higher levels of Syk and/or SHP-1 are correlated with higher likelihood of successful treatment. In embodiments, the activity levels of these proteins can be inferred by their phosphorylation state, or can be determined by amounts of the proteins, individually or together, as members of a complex of proteins involving at least Syk and SHP-1. These measurements may be compared, if desired, to the amounts in normal non-cancerous cells and/or responsive cancerous cells that have been activated by the CD-33 binding agent, or such cells that have not been activated by the CD-33 binding agent, in order to determine a base-line level of activation or non-activation against which to compare the test cells.

In view of the methods of identifying and prognosing patients for the likelihood of responsiveness to a particular cell-killing agent, the present invention provides another method of treating a patient for a neoplasia. The method comprises determining the activity state of the Syk and/or SHP-1 protein in a target neoplastic cell, and providing a treatment regimen based on the activity state that is determined. Where it is found that the levels of activity of both of these proteins is within a normal range (for example, as compared to the levels of the active proteins in cells of the same type that are known to be responsive to the cell-killing agent), a treatment regimen using the cell-killing agent of choice, alone, is implemented. Where it is found that the level of activity of one or more of these proteins is below the normal range (for example, as compared to the levels of the active proteins in cells of the same type that are known to be responsive to the cell-killing agent), a treatment regimen using the cell-killing agent of choice and a substance that increases the amount of active Syk and/or SHP-1 (whichever was found to be deficient) is implemented.

In another aspect, the invention provides compositions. The compositions can comprise at least one substance that increases the amount of active Syk protein in a cell, at least one substance that increases the amount of active SHP-1 protein in a cell, or any combination of such substances. The compositions can also comprise at least one neoplastic cell-killing agent that targets the CD33 cell-surface protein, such as an antibody that specifically targets CD33. The compositions can further comprise pharmaceutically acceptable carriers, binders, and the like, or biologically safe substances, such as salts, aqueous solvents, and the like.

In yet another aspect, the invention provides at least one container that contains the substance that is capable of increasing the amount of active Syk and/or SHP-1 in a cell. The invention also provides at least one container that contains a substance that initiates a biological response resulting in death of a cell (i.e., a cell-killing agent that targets CD33). Thus, the invention provides containers that contain compositions of the invention. In embodiments, two or more containers are combined in a kit.

BRIEF DESCRIPTION OF THE DRAWINGS

The accompanying drawings, which constitute a part of this specification, provide details on at least one embodiment of the invention and, together with the written description, serve to explain some underlying principles and embodiments of the invention.

DETAILED DESCRIPTION OF EMBODIMENTS OF THE INVENTION

Figure 1:
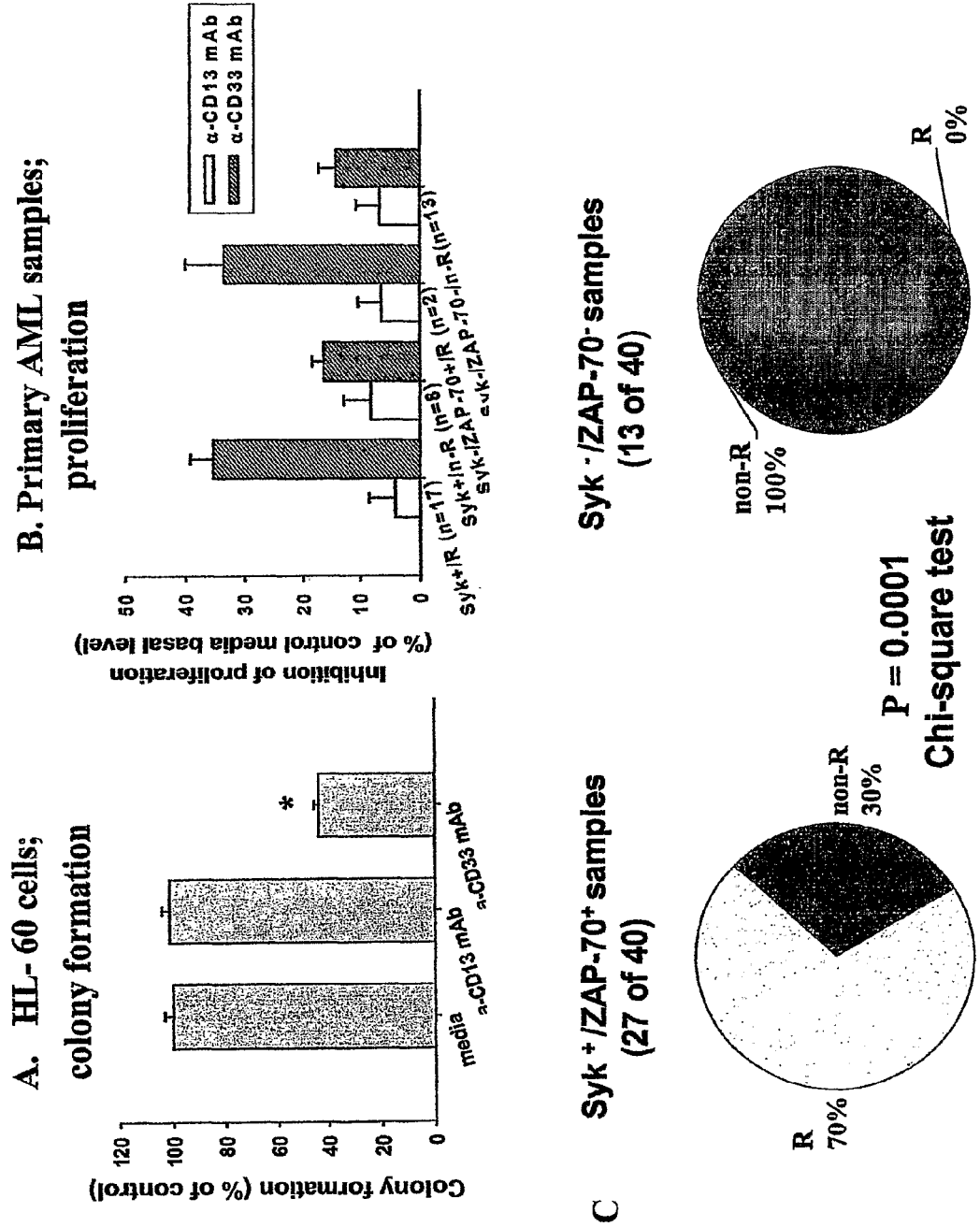
FIG. 1 shows the inhibitory effect of anti-CD33 monoclonal antibodies on neoplastic cells. Panel A is a colony forming assay of HL-60 cells. Panel B is cell proliferation assay of primary AML cells. Panel C is a pie chart showing the correlation between responders and active Syk or ZAP-70.

Reference will now be made in detail to various exemplary embodiments of the invention. It is to be understood that the following detailed description is provided to further explain details of various embodiments of the invention, and is not provided as an exhaustive description of all substances that can be used according to the invention, or all steps that can be performed in practicing the methods of the invention. Rather, it is provided to describe certain details of embodiments of the invention, which will provide those of skill in the art a more thorough understanding of various embodiments, which can be applied to other embodiments of the aspects of the invention, without requiring those artisans to practice undue experimentation to achieve the full scope of the claimed invention.

As discussed above, broadly speaking, the present invention addresses low rates of specific neoptastic cell killing seen in current treatments for neoplasias, and particularly for non-solid tumors treated with agents that target the CD33 cell-surface protein. (Note that, in this document, "neoplasia", "tumor" or "tumor cell" and "cancer" or "cancer cell" are used interchangeably as equivalent terms.) The invention addresses the low specific killing rates by providing a method of improving the killing efficacy of certain treatments by treating a patient with a substance that increases the amount of active Syk and/or SHP-1 protein in the target tumor cells before, during, or after treatment with an agent that specifically induces a cell-killing response that involves active Syk protein, SHP-1 protein, or both. In its more basic form, the present invention relates to a method of increasing the amount of active Syk and/or SHP-1 protein in a cell. This basic form of the invention is particularly relevant to methods of treating tumors that involve active Syk and/or SHP-1 protein at some point, or in methods of identifying and quantifying the effects of substances as anti-cancer agents. Thus, the present invention provides methods of treatment of tumor cells with agents that increase the expression of Syk and/or SHP-1, or that increase the amount of active Syk and/or SHP-1 in a cancer cell, where such treatments can improve the efficacy of treatments that target protein activation cascades in which Syk and/or SHP-1 is a member, such as those involving ligation of the cell-surface protein CD33.

In accordance with the invention, any cell that expresses CD33 and does not express active Syk, SHP-1, or both when the CD33 is activated by an agent that would otherwise kill the cell can be used in or treated by the methods of the invention. Thus, CD33+ cells that normally express a detectable level of active, phosphorylated Syk in response to activation of a signalling cascade by binding of an agent to CD33, but fail to express the active protein in a disease state, such as in a non-responsive cancerous state, can be included in the methods of the invention. In a similar way, cells that normally express a detectable level of active, phosphorylated SHP-1 in response to activation of a signalling cascade by binding of an agent to a CD33 protein, but fail to do express the active protein in a disease state, such as in a non-responsive cancerous state, can be included in the methods of the invention.

In view of the cells that are useful as targets in the methods of the invention (i.e., cells expressing CD33), as disclosed above and below, the invention can be used within the context of numerous neoplasias and other diseases and disorders. Non-limiting examples of the diseases and disorders that are envisioned as encompassed by this invention are typically found among non-solid tumors. Non-limiting examples of such tumors are: leukemias, such as acute myeloid leukemia (AML), chronic myeloid leukemia (CML), and acute lymphocytic leukemia (ALL). Another non-limiting example of a disease or disorder for which cells are encompassed by the present invention is MDS.

In a first aspect, the invention provides a method of increasing the amount of functionally active Syk protein kinase in a cell. The method of this aspect of the invention comprises exposing the cell, either externally or internally, to a suitable substance for a sufficient amount of time to achieve the desired effect or level of effect. Increasing the amount of active Syk protein in a cell can be accomplished through two major ways. The first way is by affecting the amount of Syk protein in a target cell. Preferably, the amount is increased. Increasing the amount of Syk protein in a target cell can be accomplished by various techniques, for example, by increasing the amount of expression of the syk gene, by stabilizing the syk mRNA, or by improving the process of or stabilizing the nascent Syk protein during initial folding. The second way is by affecting the level of activity of Syk protein in a target cell. Preferably, the activity is increased. It is known that Syk protein kinase is activated by phosphorylation. Thus, increasing the activity of Syk protein in a cell can comprise treating the cells with a substance that increases the amount of phosphorylation of the Syk protein. Numerous substances that increase phosphorylation of cellular proteins, including Syk, are known in the art, and any of these compounds can be used in accordance with the invention.

The method of increasing the amount of active Syk protein can be performed in vitro or in vivo. Techniques for exposing cells to biologically active agents in vitro and in vivo are well known to those of skill in the art, and thus need not be detailed here. Any suitable technique may be used in this invention without undue or excessive experimentation. The method can be practiced in vivo or in vitro, to provide a variety of useful methods, including, but not limited to, research methods, diagnostic and clinical methods, and therapeutic methods.

When practiced in vitro, the method of this aspect of the invention can be used to increase the responsiveness of the treated cells to cell killing by substances that activate the cell-killing cascade involving Syk. For example, because Syk is involved in cell death resulting from ligation of CD33 on tumor cells, increasing the amount of active Syk in CD33-expressing cells can render those cells more responsive to anti-cancer compounds that target CD33. Thus, the in vitro methods can be used to screen for compounds that have anti-cancer properties. In addition, because treatment to increase active Syk results in an increase in the inhibition of cells to anti-cancer compounds, the in vitro methods can be used to re-screen compounds that have either been previously rejected as insufficiently active against certain cancers, or to re-screen compounds that are known to be active against certain cancers, but thought to have low activity.

Thus, in embodiments, the present invention provides a method for detecting or identifying anti-cancer substances (i.e., drugs) that are effective in converting cells that are refractory to one or more anti-cancer agents that target the CD33 protein to cells that are sensitive to such agents. The method comprises exposing a cell that is not killed by one or more anti-cancer agents that target the CD33 protein to at least one substance, and determining the presence of phosphorylated Syk protein in the cell. The method can further comprise determining the presence of phosphorylated Syk protein in the cell prior to exposure to the substance(s), and, if desired, comparing the level of phosphorylated Syk in the cells prior to and after treatment. The presence of phosphlorylated Syk in treated cells indicates that the cell has been exposed to at least one substance that can be used as a drug for treatment of cells that are refractive to one or more agent that targets the CD33 protein to initiate a cell-killing pathway. Where the cell is exposed to a composition comprising more than one substance in the method, the method can be repeated with fewer, or even one, substance, in order to identify the active substance(s) within the composition. In certain embodiments, the method comprises detecting phosphory-lated Syk protein as an independent protein. In other embodiments, the method comprises detecting phosphorylated Syk protein as a member of a complex involving SHP-1. Detecting or determining the presence of active, phosphorylated Syk can be through any of a number of well-known techniques, such as by Western blotting or other immunoassays. Determining can also be through indirect methods, such as by detecting Syk-specific mRNA. In embodiments where detecting is based on Syk protein, detecting can be through detection of the protein, per se, or through detection of phosphorylated residues or peptides. Where the methods are methods of identifying substances, the substances that are found to be active can be identified based on structural features, and such identification can be performed before exposing the substance(s) to the cell(s) (e.g., by exposing the cell(s) to known compounds) or after (e.g., by exposing the cells to a mixture of undefined or incompletely defined compounds, then chemically defining the active compound(s) when one or a few are found to be active).

Accordingly, the invention provides a method of detecting or identifying anti-cancer drugs that treat cancers that are refractive to agents that target the CD33 protein. Thus, the invention provides a method of detecting or identifying drugs that treat cancers that are refractive to anti-CD33 antibody treatments. While it is envisioned that the drugs may be effective at treating the cancer alone, it is also envisioned that the drugs will be advantageously used in combination with one or more agent that targets the CD33 protein.

As discussed in more detail below, when practiced in vivo, the method can be a method of treating a subject, patient, person, or individual (all of which being used interchangeably herein), and thus represents a different aspect of the invention. This aspect of the invention is, at its basic level, a method of increasing the presence of functional Syk protein in cells of a patient suffering from cancer. In general, the method comprises administering to a patient suffering from at least one type of tumor or cancer in which cancerous cells express the CD33 protein on the cell surface, such as one suffering from a non-solid tumor, an amount of at least one substance capable of increasing the amount of active Syk protein in at least one cell of the tumor or cancer. Administering the substance results in an improvement in the responsiveness of the patient's cancer or tumor cells to cell-killing agents (also referred to herein as cell-killing substances and chemotherapeutic agents or substances) that target the CD33 protein.

Within the context of the invention, exposing cells can take a number of forms. For example, when the method is practiced in vitro, exposing can be accomplished by adding the selected substance to cells growing or being maintained in a culture environment, such as a culture bottle, plate, or other standard growth container. While the substance can be directly added to the surface or interior of the cells of interest, it will more commonly simply be added to the medium in which the cells are being cultured. In the event that overexpression of one or more of the proteins is desired for research purposes, the step of exposing can include transforming or transfecting one or more cell with nucleic acid encoding the substance of interest, and permitting the exposed cell to express the substance. On the other hand, when the method is practice in vivo, exposing can be by any known technique that is known as effective for delivering substances to living cells of a multicellular organism. Thus, it can be by way of injection into a site containing the cells of interest, injection or infusion into the blood stream of the subject, inhalation, etc.

Those of skill in the relevant arts are well aware of the amounts to use for exposure and the amounts of time to continue the exposure.

Methods of detection of Syk and SHP-1 are well known to those of skill in the arts of cancer research and therapy. Any of the known techniques can be used, each method being selected by the individual practitioner based on any number of parameters, including, but not limited to: personal preference; availability of reagents, substrates, and equipment; cost; time; and safety requirements of his institution. Examples of suitable detection methods include, but are not limited to: immunological methods, such as Western Blotting, immunoprecipitation (IP), co-immunoprecipitation (co-IP), enzymatic assays (e.g., kinase and phosphatase assays), nucleic acid detection assays (e.g., PCR), and cell detection assays (e.g., flow cytometry). According to the invention, any detectable, significantly significant change in active Syk and/or SHP-1, using any suitable technique, is sufficient to provide the level of increase envisioned by the invention.

In one embodiment, the invention provides a method of increasing the presence of functional Syk protein in cells of a patient suffering from a neoplasia characterized by cells that express CD33 on their surfaces. In general, the method comprises administering to a patient suffering from at least one such neoplasia an amount of at least one substance capable of increasing the amount of active Syk protein in at least one neoplastic cell of the patient. The method results in improving the responsiveness of the patient's neoplastic cells to cell-killing agents that target the CD33 protein, and that can be administered in addition to the active Syk-increasing substance. These agents can be administered before, during, and/or after administration of the active Syk-increasing substance. In preferred embodiments, the substance(s) are administered in amounts sufficient to raise the level of active Syk protein in neoplastic cells to amounts substantially the same as the amounts seen in cells of the same type that are sensitive to agents that target the CD33 molecule. In preferred embodiments, the substance(s) increase the amount of active SHP-1 protein as well, preferably to an amount substantially the same as the amounts seen in cells of the same type that are sensitive to agents that target the CD33 molecule.

In embodiments, the amount of functional Syk protein is increased in a neoplastic cell by exposure of the cell to one or more demethylating or hypomethylating (these terms are used interchangeably) agents. It has been found that the effect of hypomethylating agents is to increase the amount of active Syk protein in cells, with the ultimate effect of up-regulating a signalling pathway involving Syk, which ultimately leads to cell death. Any suitable hypomethylating agent may be used in accordance with the invention. In particular embodiments, 5-Azacytidine (azacytidine; 5-Aza-CR) or a structurally related compound is used. For example, in some embodiments, 5-Aza-2'-deoxycytadine (decitabine; DAC; 5-Aza-CdR) is used. In other embodiments, 5,6-dihydro-5-azacytidine is used. In yet other embodiments, procaine or a structurally-related compound, such as procainamide, is used. Further, in other embodiments, (−)-egallocatechin-3-gallate (EGCG) is used. Other embodiments relate to the use Zebularine. Other hypomethylating agents may be known to those of skill in the art, and may be used in accordance with the present invention. In embodiments, a combination of two or more hypomethylating agents are used.

In preferred embodiments, active Syk protein levels are increased in at least one cell that has previously been found to be refractive to at least one anti-neoplastic treatment. For example, active Syk protein levels can be increased in a neoplastic cell that has survived prior treatment with one or more anti-neoplastic agents. In certain of these embodiments, active SHP-1 protein levels are also increased.

Yet another aspect of the invention provides a method of increasing the amount of functionally active SHP-1 protein kinase in a cell. Details and characteristics of increasing the amount of active SHP-1 in a cell that are not discussed herein can be understood to be the same or substantially the same as those discussed above with respect to Syk. In general, the method comprises exposing the cell, either externally or internally, to a suitable substance for a sufficient amount of time to achieve the desired effect or level of effect on the SHP-1 protein. As with affecting the level of active Syk protein in a cell, the substance can act at the level of transcription, for example by increasing the amount of expression of the gene encoding SHP-1. Alternatively, it can act at the level of translation by stabilizing the SHP-1 mRNA or otherwise increasing the amount of SHP-1 protein produced from mRNA. In addition, it can act post-translationally, by, for example, stabilizing the SHP-1 protein kinase through post-translational modifications of the SHP-1 protein (e.g., phosphorylation or dephosphorylation at one or more sites on the protein), or by aiding in proper folding of the SHP-1 protein. Preferably, the method results in an increase in the amount or activity of the SHP-1 protein in the cell being treated.

The method of increasing the amount of active SHP-1 protein can be performed in vitro or in vivo. Techniques for exposing cells to biologically active agents in vitro and in vivo are well known to those of skill in the art, and thus need not be detailed here. Any suitable technique may be used in this invention without undue or excessive experimentation. The method can be practiced in vivo or in vitro, to provide a variety of useful methods, including, but not limited to, research methods, diagnostic and clinical methods, and therapeutic methods.

When practiced in vitro, the method of this aspect of the invention can be used to increase the responsiveness of the treated cells to cell killing by substances that activate the cell-killing cascade involving SHP-1. For example, because SHP-1 is involved in cell death resulting from ligation of CD33 on tumor cells, increasing the amount of active SHP-1 in CD33-expressing cells can render those cells more responsive to anti-cancer compounds that target CD33. Thus, the in vitro methods can be used to screen for compounds that have anti-cancer properties. In addition, because treatment to increase active SHP-1 results in an increase in the inhibition of cells to anti-cancer compounds, the in vitro methods can be used to re-screen compounds that have either been previously rejected as insufficiently active against certain cancers, or to re-screen compounds that are known to be active against certain cancers, but thought to have low activity.

Thus, in embodiments, the present invention provides a method for detecting or identifying anti-cancer substances (i.e., drugs) that are effective in converting cells that are refractory to one or more anti-cancer agents that target the CD33 protein to cells that are sensitive to such agents. The method comprises exposing a cell that is not killed by one or more anti-cancer agents that target the CD33 protein to at least one substance, and determining the presence of phosphorylated SHP-1 protein in the cell. The method can further comprise determining the presence of phosphorylated SHP-1 protein in the cell prior to exposure to the substance(s), and, if desired, comparing the level of phosphorylated SHP-1 in the cells prior to and after treatment. The presence of phosphorylated SHP-1 in treated cells indicates that the cell has been exposed to at least one substance that can be used as a drug for treatment of cells that are refractory to one or more agent that targets the CD33 protein to initiate a cell-killing pathway.

Where the cell is exposed to a composition comprising more than one substance in the method, the method can be repeated with fewer, or even one, substance, in order to identify the active substance(s) within the composition. In certain embodiments, the method comprises detecting phosphorylated SHP-1 protein as an independent protein. In other embodiments, the method comprises detecting phosphorylated SHP-1 protein as a member of a complex involving Syk, and in particular, phosphorylated, active Syk.

Detecting or determining the presence of active, phosphorylated SHP-1 can be through any of a number of well-known techniques, such as by Western blotting or other immunoassays. Determining can also be through indirect methods, such as by detecting SHP-1-specific mRNA. In embodiments where detecting is based on SHP-1 protein, detecting can be through detection of the protein, per se, or through detection of phosphorylated residues or peptides. Where the methods are methods of identifying substances, the substances that are found to be active can be identified based on structural features, and such identification can be performed before exposing the substance(s) to the cell(s) (e.g., by exposing the cell(s) to known compounds) or after (e.g., by exposing the cells to a mixture of undefined or incompletely defined compounds, then chemically defining the active compound(s) when one or a few are found to be active).

Accordingly, the invention provides a method of detecting or identifying anti-cancer drugs that treat cancers that are refractive to agents that target the CD33 protein. Thus, the invention provides a method of detecting or identifying drugs that treat cancers that are refractive to anti-CD33 antibody treatments. While it is envisioned that the drugs may be effective at treating the cancer alone, it is also envisioned that the drugs will be advantageously used in combination with one or more agent that targets the CD33 protein.

As discussed in more detail below, when practiced in vivo, the method can be a method of treating a subject, patient, person, or individual, and thus represents a different aspect of the invention. This aspect of the invention is, at its basic level, a method of increasing the presence of functional SHP-1 protein in cells of a patient suffering from cancer. In general, the method comprises administering to a patient suffering from at least one type of tumor or cancer in which cancerous cells express the CD33 protein on the cell surface, such as one suffering from a non-solid tumor, an amount of at least one substance capable of increasing the amount of active SHP-1 protein in at least one cell of the tumor or cancer. Administering the substance results in an improvement in the responsiveness of the patient's cancer or tumor cells to cell-killing agents that target the CD33 protein.

In one embodiment, the invention provides a method of increasing the presence of functional SHP-1 protein in cells of a patient suffering from a neoplasia characterized by cells that express CD33 on their surfaces. In general, the method comprises administering to a patient suffering from at least one such neoplasia an amount of at least one substance capable of increasing the amount of active SHP-1 protein in at least one neoplastic cell of the patient. The method results in improving the responsiveness of the patient's neoplastic cells to cell-killing agents that target the CD33 protein, and that can be administered in addition to the active SHP-1-increasing substance. These agents can be administered before, during, and/or after administration of the active SHP-1-increasing substance. In preferred embodiments, the substance(s) are administered in amounts sufficient to raise the level of active SHP-1 protein in neoplastic cells to amounts substantially the same as the amounts seen in cells of the same type that are sensitive to agents that target the CD33 molecule. In preferred embodiments, the substance(s) increase the amount of active Syk protein as well, preferably to an amount substantially the same as the amounts seen in cells of the same type that are sensitive to agents that target the CD33 molecule.

In embodiments, the amount of functional SHP-1 protein is increased in a neoplastic cell by exposure of the cell to one or more demethylating or hypomethylating agents. It has been found that the effect of hypomethylating agents is to increase the amount of active SHP-1 protein in cells, with the ultimate effect of up-regulating a signalling pathway involving SHP-1, which ultimately leads to cell death. Any suitable hypomethylating agent may be used in accordance with the invention. In embodiments, the hypomethylating agents mentioned above are used. Other hypomethylating agents may be known to those of skill in the art, and say be used in accordance with the present invention. In embodiments, a combination of two or more hypomethylating agents are used.

In preferred embodiments, active SHP-1 protein levels are increased in at least one cell that has previously been found to be refractive to at least one anti-neoplastic treatment. For example, active SHP-1 protein levels can be increased in a neoplastic cell that has survived prior treatment with one or more anti-neoplastic agents. In particular, active SHP-1 protein levels can be increased in cells that have survived treatment with one or more agent that targets the CD33 protein. In certain embodiments, active Syk protein levels are also increased.

As a general matter, the substance can be any of a variety of molecules, which can act at a variety of points in the production of active proteins. Thus, in embodiments, the substance acts at the nucleic acid level, such as at the level of transcription or mRNA stability. For example, the substance can be a DNA methylation inhibitor or a DNA demethylating agent. Examples of such substances include, but are not limited to, 5-azacytidine. Alternatively, the sub stance can be a small molecule transcription activator that binds to DNA or DNA-binding proteins to activate transcription of genes, either specifically (e.g., blood cell specific proteins), semi-specifically (e.g., biological response cascade proteins), or non-specifically. Furthermore, it can be a nucleic acid construct that comprises all or part of the syk gene and/or the SHP-1 gene, which can be delivered to the cell for transient expression by any suitable method known in the art for delivering nucleic acids to cells in vitro or in vivo. Examples of such delivery methods include the use of electroporation or calcium phosphate for in vitro delivery, and targeting delivery using antibody bound liposomes for in vivo delivery.

In embodiments, the substance acts at the level of RNA transcription or DNA replication. For example, it can be a substance that interferes with one or both of these activities. Alternatively, it can act to modify DNA such that transcription or replication is enhanced.

In embodiments, the substance acts at the level of translation. For example, the substance can act by stabilizing the syk mRNA and/or the SHP-1 mRNA, or otherwise increasing the amount of Syk and/or SHP-1 protein produced from mRNA.

In yet other embodiments, the substance acts post-translationally. For example, it can act to stabilize or activate the Syk protein kinase through post-translationally. For translational modifications of the Syk protein (e.g., phosphorylation or dephosphorylation at one or more sites on the protein), by aiding in proper folding of the Syk protein, or by stabilizing interactions between the active Syk protein and proteins to which it binds during the cascade of events leading to cell death, or by de-stabilizing protein interactions that do not facilitate cell death. Likewise, the same functions can be provided within the context of expression of active SHP-1.

In one embodiment, the substance that increases the level of active Syk and/or SHP-1 protein is a nucleic acid that comprises sufficient information to encode one or more of these proteins. In this embodiment, administration comprises delivering the nucleic acid to at least one tumor cell in the patient, and expressing the nucleic acid to provide active encoded protein in the cell. Numerous techniques for delivering nucleic acids to cells in vitro and in vivo are known, and any such technique can be used in accordance with this embodiment of the invention. For example, techniques such as transfection and transformation can be used in vitro. In addition, for example, delivery can be accomplished by capturing the nucleic acid in a liposome that comprises antibodies on its surface, where the antibodies are specific for one or more proteins on the surface of cancer cells of a cancer to be treated. Upon administration of the liposomes, the liposomes specifically bind to the cancer cells and deliver the nucleic acid to the cells. Once inside the cells, the nucleic acids can, but are not necessarily, integrated into the host cell genome. Whether integrated into the host genome or maintained transiently as an extra-genomic entity, the nucleic acid is transcribed and the resulting mRNA is translated by the normal cellular machinery, resulting in production of an active protein.

Because the effects of the substance can be at many levels, there is no overall structural requirement for the substance. That is, because the substance can be any of a number of molecules, each having a different structure, it is not possible to define a core structure that provides the function of producing an active Syk and/or SHP-1 protein. However, because these proteins are widely studied and well understood, and because the exemplary substances that can be used in accordance with the methods of the invention are well-known and structurally and functionally characterized, one of skill in the art can identify substances that provide the stated function without undue experimentation. For example, because it has been found that 5-azacytidine can function to increase the level of active Syk and SHP-1 proteins in cells, one of skill in the art would understand that other functionally, but not necessarily structurally, related hypo-methylating agents could be used in accordance with the present invention.

The methods of increasing active Syk and/or SHP-1 can further comprise exposing the cell to (e.g., administering to a patient) at least one other substance that initiates a biological response resulting in death of a cell, where the biological response involves active Syk and/or SHP-1 protein at one or more steps. For clarity of reference, this other substance is referred to herein as a cell-killing agent or simply an agent. The cell-killing agent can be any substance that binds to CD33 and can initiate a biological response resulting in death of a cell, where the biological response involves active Syk and/or SHP-1 protein at one or more steps. For example, the cell killing agent can be one that binds to CD33 and initiates a cascade of biological and biochemical activities that result in cell death, particularly through apoptosis. Many antibodies are known that specifically bind CD33 on the surface of cells. Because the effect of all of these antibodies appears to be to ligate CD33 proteins and initiate a cascade of events resulting in cell death, any antibody that binds CD33 can be used as the cell-killing agent. Indeed, CD33-specific immunotoxins and immunoconjugates (such as Mylotarg®, Wyeth), which presumably act to kill cancer cells in ways other than simple ligation of CD33 and initiation of an apoptosis cascade, can be used as well as naked antibodies. Other antibodies or substances that specifically bind to particular cell-surface proteins on neoplastic cells are known, and each of these can be used in accordance with the invention.

As used herein, the term antibody is used generally to include all forms of immunoglobulins and their fragments. Thus, it encompasses immunoglobulins of all classes from all species. It includes monoclonal antibodies as well as polyclonal antibodies. It includes naked antibodies as well as those having bioactive moieties grafted to them. In embodiments where antibodies are described as anti-CD33 antibodies, such antibodies are defined as antibodies that are capable of binding CD33, as measured in any standard antibody-antigen or ligand-receptor assay, which are well known to those of skill in the art and thus need not be detailed here. This definition applies to all of the various forms of antibodies encompassed by the term.

The term antibody thus encompasses chimeric antibodies, in which one portion of the antibody peptide chain comprises amino acids from one source species and another portion of the antibody peptide chain comprises amino acids from another source. Chimeric antibodies also encompass molecules that are formed from three or more source molecules. Such antibodies can be made by protein fusions, but are preferably made by way of fusions of coding sequences of nucleic acids, then expression of the resulting fusion (or chimeric) nucleic acid. The concept of chimeric antibodies, as well as techniques for designing and making them, are standard concepts in the art, and can be practiced by those of skill in the art without undue experimentation.

The broad term antibody also encompasses humanized antibodies. As used herein and in the art in general, a humanized antibody comprises an antibody in which the framework and constant regions are of human origin or are engineered to comprise human or human-like sequences. At the same time, the variable region or the complementary determining region (CDR) can have a sequence derived from another species, such as a mouse or rabbit. In this way, a specific antibody can be identified in a non-human species, but used in humans while avoiding anti-antibody immune reactions in the recipient human patient. The concept of humanized antibodies, as well as techniques for designing and making them, are standard concepts in the art, and can be practiced by those of skill in the art without undue experimentation.

The term antibody also encompasses immunoconjugates and immunotoxins. Immunoconjugates, as known in the art, comprise antibodies and therapeutic agents, where the two are covalently linked via suitable groups, such as one or more oxidized carbohydrate groups and one or more amine groups. Immunotoxins are likewise conjugates of antibodies and bioactive agents, and in particular, toxic compounds that can be used to kill cells to which the antibody portion binds. The concept of immunoconjugates and immunotoxins, as well as techniques for designing and making them, are standard concepts in the art, and can be practiced by those of skill in the art without undue experimentation. One particular immunotoxin of interest to the present invention is Mylotarg® (Wyeth).

Antibodies can also be antibody fragments. Included among these are fragments that can be generated by protease digestion of antibodies, or fragments that can be generated by molecular biology techniques. For example, antibodies can be antibody fragments such as $F_v$, Fab, and $F(ab')_2$. They also can be single-chain antibodies, antibodies comprising just the CDR or essentially just the CDR. In general, antibody fragments can be any of the antibody fragments known to those of skill in the art. Such antibody fragments can be designed and made without undue or excessive experimentation.

In addition, because in embodiments the effect of the combination therapy of the invention is particularly strong when the cell-killing agent specifically interacts with CD33 on the cell surface, any substance that binds and ligates CD33 molecules is preferred in these embodiments as the cell-killing agent. That is, in these embodiments the cell-killing agent that binds to CD33 is not limited to anti-CD33 antibodies, but can be any substance that binds to, and activates CD33.

The general method of the invention comprises exposing at least one cell to at least one substance or agent. In in vivo aspects, the step of exposing comprises administering the substance(s) and/or agent(s) to a subject in need of them. The amounts administered are amounts sufficient to achieve a therapeutic effect, such as to increase the amount of active Syk and/or SHP-1 protein in at least one cell of the subject. In these aspects, administering can be achieved by any known technique. Numerous techniques for administering substances systemically to the blood system of humans and animals is known, and any one can be used. For example, administration can be through bolus injection of the substance into a vein or artery, administration over minutes or hours by way of intravenous infusion, or oral administration by way of liquid or solid (e.g., tablet, capsule, powder). It can also be accomplished by injection to specific sites of the body (e.g., i.p. injection) or diffusion through skin or mucous membranes (e.g., through a patch or dissolvable lozenge or the like). Those of skill in the art are free to select the most appropriate route of administration for the particular subject and cancer, and such choice will not represent undue experimentation.

Amounts of chemotherapeutic substances to be administered to patients are well known to those of skill in the art, and appropriate amounts to be administered in accordance with the present invention can be determined without excessive experimentation. As a general rule, chemotherapeutic substances can be administered to subjects in therapeutically effective amounts. Those amounts generally range from about 0.01 $g/m^2$ of body area to about 30 $g/m^2$ body area, and can be administered over any amount of time, such as a short period (about 6 hours or less) or a much longer period (about 96 hours or longer) through continuous infusion. Dosing regimens can include considerably longer times, such as two weeks, one month, or more. In these long dosing regimens, doses of the chemotherapeutic substance(s) can be relatively short (e.g., the entire dose being administered in one to several hours), and the doses repeated at regular intervals, such as daily, once weekly, twice weekly, or at other intervals. Various chemotherapeutic dosing regimens are known to those of skill in the art, and any suitable regimen can be used. For example, where the substance is 5-azacytidine, the dose can be 75 $mg/m^2$. A dosing regimen can include a daily dosing of this amount for 5-7 days.

Where treatment comprises administering one or more antibodies, it will generally be administered in an amount from about 0.1 $mg/m^2$ of the patient's body area to about 15.0 $mg/m^2$ body area. For example, where Mylotarg® (Wyeth) is administered, it can be administered at 9 $mg/m^2$ or about that amount by injection. Injections can be administered at days 1 and 14 of a treatment regimen. As an additional non-limiting example, naked anti-CD33 antibody can be administered in a regimen comprising two treatment cycles. In the first cycle, the antibody can be administered at exactly or about 12 $mg/m^2$ daily for 4 days. In the second cycle, the antibody can again be administered at exactly or about 12 $mg/m^2$ at 10-12 days after completion of the first cycle.

In view of the complementary effect of the CD33-targeting agent and the substance that affect the presence and level of active Syk and/or active SHP-1, treatment regimens according to the invention can comprise administration of the bioactive agents and substances at amounts that are less than would be administered in regimens comprising administering the agents and substances alone. Thus, for example, a treatment regimen comprising co-administration of Mylotarg® (Wyeth) with a Syk– and/or SHP-1-activating substance can comprise administering the immunotoxin at about one-half or less of the amount typically administered in a regimen in which it is the sole bioactive agent. For example, it can be administered at 50% of its typical amount, at 60% of its typical amount, at 75% of its typical amount, at 80% of its typical amount, or at 90% of its typical amount.

Alternatively, dosing regimens can be shortened in a co-therapy according to the present invention. For example, a treatment regimen comprising administration of 5-azacytidine can be shortened from 5-7 days to 3 days or fewer, such as 2 or even only one day.

By reducing the amount of bioactive agents administered to patients or reducing the length of the treatment regimen, toxicity to the patient or other side-effects of treatment can be reduced. It also can reduce the cost of treatment regimens.

Although typical amounts and treatment regimens are presented for exemplary purposes, one should understand that particular substances and agents might be typically used outside of the general ranges presented above, and one should use each particular substance or agent in an amount that is suitable for the specific substance or agent. Those of skill in the art are cognizant of the various parameters to take into account in devising a particular treatment regimen for a patient, and devising individualized treatment regimens for particular patients is well within the skill of those of skill in the art. Accordingly, the present invention encompasses both in vitro assays/methods and in vivo treatment methods. The particular amount of antibody to be used in the various methods can be determined by those of skill in the art without undue experimentation, based not only on the typical amounts used in the art, but on the examples provided herein. As a general rule, for in vivo treatments, the antibodies are administered in therapeutically effective amounts.

As discussed above, the methods of the present invention are based, at least in part, on the discovery that neoplastic cells that are refractory to treatments based on binding of a cell-killing agent to CD33 can be made responsive to that agent by increasing the level of active Syk and/or SHP-1 protein in the cell. While not being limited to any particular mechanism of action, it is believed that these two proteins are involved in a common signalling pathway that leads ultimately to death of the cell that is exposed to the cell-killing agent. Under this scheme, cells that are refractory to the cell-killing agent have that quality not because the cell-killing agent is unable to exert its effect on its target, but because a cell death signalling pathway that involves active Syk and/or SHP-1 is interrupted by the absence of a sufficient amount of an active form or one or both of these proteins. Returning the cells to a more normal level of one or more of these active proteins supplies the missing element(s) for the signalling cascade/pathway, and returns the cell to a responsive state that renders the cell sensitive to the cell-killing agent.

Accordingly, the present invention provides a method of treating a patient suffering from a neoplasia, such as those suffering from a tumor or a cancer. The method comprises administering to a patient suffering from a neoplasia at least one substance capable of increasing the amount of active Syk, SHP-1, or combinations of both of these proteins in at least one neoplastic cell that expresses CD33 on its surface. The substance is administered in an amount that is sufficient to increase the amount of active Syk and/or SHP-1 in a target neoplastic cell a detectable amount. Preferably, the substance is administered in an amount that is sufficient to cause the neoplastic cell to die. In embodiments, the substance is administered in an amount that is sufficient to render at least one target neoplastic cell responsive to a cell-killing agent other than the substance. For example, where the target cell is a cell that is refractory to an antibody-based cell killing agent that kills cells by binding to CD33, administration of the substance prior to or concurrently with the antibody renders the target cell responsive to the antibody agent.

Thus, in embodiments, the method can further comprise administering at least one agent, which is a different molecule than the substance that increases active Syk and/or SHP-1, that initiates a biological response resulting in death of a cell. In preferred embodiments, the biological response involves active Syk and/or SHP-1 protein at one or more steps. The method is particularly advantageously practiced on patients who have previously failed to respond to treatments based on administration of the agent or substance alone. In certain embodiments, the method is practiced on patients who have previously failed to respond to treatments based on administration of an antibody that targets CD33.

The method of treating a subject can comprise administering to the subject a sufficient amount of a substance that increases the amount of active Syk and/or SHP-1 protein, and further comprises administering to the same subject at least one cell-killing agent that targets the CD33 protein. Administration of the substance and cell-killing agent can be accomplished by any known technique and according to any suitable route and dosage, in accordance with the discussion above. Accordingly, the method can be a combination therapy for cancer. The cell killing agent can be administered before, at the same time, or after administration of the substance that increases active Syk and/or SHP-1 levels in cells. The cell-killing agent is administered in an amount sufficient to kill at least one cell of at least one tumor affecting the subject. In embodiments, administration of the substance that increases the level of active Syk and/or SHP-1 in cells reduces the amount of cell killing agent that must be administered to the subject (as compared to the amount needed in the absence of administration of the substance that increases active Syk and/or SHP-1 levels). Thus, in embodiments, the method of treating is also a method of improving the efficacy of one or more cell-killing agents in killing cancer cells. In view of the lower doses potentially needed, it also may be a method of reducing the toxic side-effects of a treatment regimen for a neoplasia. As mentioned above, the substance and cell-killing agent can be administered at the same time or one before the other. The method can also comprise multiple administrations of the substance, the cell-killing agent, or both. Thus, the method of the invention contemplates various treatment regimens. The treatment regimen to be used on any particular subject will depend on the type of cancer, the stage of development of cancer, and other factors, such as age, general health, and the like. It is well within the skill of those of skill in the art to select the appropriate treatment regimen without undue experimentation.

Accordingly, the present invention provides a method of treating a patient suffering from a tumor or cancer characterized by cells that express CD33. The method comprises administering at least one substance capable of increasing the amount of active Syk and/or SHP-1 protein in at least one cell of the tumor or cancer. The method can further comprise administering at least one cell-killing agent that targets CD33. The cell-killing agent preferably is one that initiates a biological response resulting in death of a cell, where the biological response involves active Syk and/or SHP-1 protein at one or more steps. In embodiments, the method comprises administering at least one substance capable of increasing the amount of active Syk and/or SHP-1 protein in a cancer cell, and administering at least one anti-CD33 antibody. In preferred embodiments, the substance is 5-azacytidine. In other preferred embodiments, the substance is another hypomethylation agent.

The method of treating a neoplasia can be used to treat any neoplasia that involves a pathway leading to cell death that involves the Syk and/or SHP-1 proteins and binding of an agent to the CD33 protein. The present inventors have discovered that the presence of active forms of these proteins in a cancer cell expressing CD33 can increase the susceptibility of the cell to CD33 protein binding agents, such as anti-CD33 antibodies. The inventors have further discovered that artificially increasing the levels of active forms of these proteins in such cells increases the killing efficacy of the cell-killing agents, such as anti-CD33 antibodies and anti-CD33 immunotoxins and immunoconjugates.

In one aspect, the invention provides a method of increasing the efficacy of a treatment for a neoplasia, where the treatment is based, at least in part, on killing of neoplastic cells by binding of an agent to CD33. Certain current or proposed methods of treating neoplasias involve binding of cell-killing agents to CD33. At least part of the killing action of these agents is thought to be due to the binding of the agent to the protein, which sets off a signalling cascade within the cell that ultimately leads to cell death, often through the process of apoptosis. However, a certain number of neoplastic cells in patients are often found to be resistant to the cell-killing action of the agent. The present invention recognizes, for the first time, that failure of these cells to respond to the cell-killing agent is due to a defect in the signalling cascade, and in particular, to a deficiency in the presence or amount of active Syk and/or SHP-1. According to the present invention, the efficacy of anti-cancer treatments based on cell-killing agents that bind to CD33 proteins on the surface of neoplastic cells can be increased by including in the treatment administration of a substance that increases the amount and/or activity of Syk and/or SHP-1. By doing so, sufficient levels of active Syk and/or SHP-1 are present in the neoplastic cells, the signalling pathway is restored, and the cell-killing agent becomes effective against these previously refractory cells.

Thus, the present invention provides a method of improving the efficacy of a treatment for a neoplastic disease. The method comprises co-administering to a patient suffering from a neoplasia 1) at least one substance in an amount that is sufficient to increase the amount, activity, or both of active Syk, SHP-1, or both of these proteins, and 2) a cell-killing agent that targets CD33 in an amount that is sufficient to result in death of at least one neoplastic cell of the patient.

In certain embodiments, the method is a method of treating a sub-population of patients for a neoplasia, where the sub-population are patients who fail to respond to a treatment for the neoplasia that is based on use of a cell-killing agent alone. In these embodiments, the method is the same as disclosed above, but is only practiced on a select group of non-responder patients. The method of this embodiment permits successful treatment of patients suffering from a neoplasia where another treatment, which is based at least in part on the same general mechanism of action, has failed.

In embodiments, the methods of increasing the amount of Syk and/or SHP-1 and the methods of treating a neoplasia can comprise assaying Syk and/or SHP-1 gene expression, Syk and/or SHP-1 protein expression, Syk and/or SHP-1 protein kinase activity, Syk and/or SHP-1 protein association with other cellular proteins, or assaying any other biological or biochemical property of the Syk and/or SHP-1 proteins. For example, it can comprise detecting and/or quantitating syk or SHP-1 gene expression using PCR, Northern blotting, and the like. Alternatively, it can comprise detecting and/or quantitating Syk or SHP-1 protein expression using SDS-PAGE analysis, Western blotting or other immunological methods of protein detection, and the like. Likewise, it can comprise detecting and/or quantitating Syk or SHP-1 protein interaction with each other or with other proteins in the cell through immunoprecipitation and the like. Other techniques known to those of skill in the art may be used as well without undue experimentation.

The present invention thus provides for the use of at least one substance capable of increasing the amount of active Syk and/or SHP-1 protein in at least one cell of a neoplasia (or neoplastic cell in culture) to make a pharmaceutical composition, and the use of the substance(s) in the treatment of at least one neoplasia. The invention further provides for the use of such substance(s) alone or in combination with at least one other substance (i.e., an agent) that initiates a biological response resulting in death of a cell, where the biological response involves active Syk and/or SHP-1 protein at one or more steps. Such a use can be for the production of a pharmaceutical composition or combination of compositions, or can be for the use in treating at least one neoplasia.

In another aspect, the invention provides methods of identifying patients who are or have a high likelihood of being refractory (non-responsive) to anti-neoplasia treatments that are based on binding of a cell-killing agent to a cell-surface protein. The method comprises obtaining at least one neoplastic cell from the neoplasia that is the target of the cell-killing agent, and determining the presence and activity level of the Syk and/or SHP-1 protein from that cell. The presence of active Syk and/or SHP-1 is indicative of the likelihood of successful treatment of the neoplasia with the cell-killing agent, where higher levels of Syk and/or SHP-1 are correlated with higher likelihood of successful treatment. Low or undetectable levels are indicative of low likelihood of successful treatment with the cell-killing agent alone. Methods of detecting active Syk and/or SHP-1 are known in the art, and need not be discussed in detail here. Non-limiting exemplary techniques are disclosed herein and include Western blotting, IP, and co-IP. Detection of mRNA can be used as an approximation of or proxy for active protein levels, but one might wish to confirm assays for mRNA levels to ensure that active protein of interest is, in fact, produced from the mRNA.

It is known that the Syk and SHP-1 proteins are phosphorylated during the process of activation of the proteins. Thus, where desired, the practitioner can determine not only the amount of these proteins that are present in the cell(s) of interest, but can determine the amount of phosphorylated protein as well. Alternatively, only the amount of phosphorylated protein might be detected. In embodiments, the activity levels of these proteins can be inferred by their phosphorylation state, or can be compared to by the relative amounts of phosphorylated protein as compared to non-neoplastic cells of the same cell type.

Sensitive techniques for detecting Syk and SHP-1, as well as many other phosphorylated proteins, are known in the art. Any suitable technique can be used in accordance with the invention. Regardless of the method used, low or undetectable levels of the protein of interest can be considered as indicative of a non-responsive state. Where techniques are used that are known to be less sensitive than others, the results can be confirmed with more sensitive assays, if desired. Preferably, a highly sensitive and specific assay, such as one based on immunological detection of the Syk or SHP-1 protein, is used.

Where the method determines that the target neoplastic cell expresses normal levels of Syk and/or SHP-1 upon binding of an agent that targets CD33, a normal treatment regimen based on use of the cell-killing agent (e.g., antibody) of choice can be initiated. On the other hand, where the method determines that the target neoplastic cell expresses below normal levels of Syk and/or SHP-1, treatment with the cell-killing agent alone should be avoided. In this way, patients are not exposed to a chemotherapeutic treatment that would be ineffective. Furthermore, the patient would not be subjected to a treatment regimen that would take weeks or months to implement, with no beneficial effect as a result.

In the event that the method determines that Syk or SHP-1 is present in low amounts or is undetectable, an alternative treatment course involving administration of a substance that increases active Syk and/or SHP-1 and the cell-killing agent (as discussed above) can be initiated. In this way, the patient (non-responder) will be immediately provided with a treatment regimen that has a higher likelihood of success than a treatment regimen that is based solely on administration of the cell-killing agent alone, and thus has a higher likelihood of survival. Among other things, this aspect of the invention permits the practitioner to identify a sub-population of cancer patients who would have a low or no response profile for a particular agent, and to design a treatment regimen that is more likely to be successful.

In yet another, related aspect, the invention provides methods of prognosing the likelihood of a patient being refractory to anti-neoplasia treatments that are based on binding of a cell-killing agent to a cell-surface protein. The method comprises obtaining at least one neoplastic cell from the neoplasia that is the target of the cell-killing agent, and determining the presence and activity level of the Syk and/or SHP-1 proteins from that cell. The presence of active Syk and/or SHP-1 is indicative of the likelihood of successful treatment of the neoplasia with the cell-killing agent, where higher levels of Syk and/or SHP-1 are correlated with higher likelihood of successful treatment. Lower levels or absence of detectable levels indicate that there is a low probability of successfully treating the neoplasia with the cell-killing agent.

As with the method of identifying patients who would be refractory to a particular treatment regimen, in embodiments, the activity levels of these proteins in the method of prognosing can be inferred by their phosphorylation state, or can be compared to by the relative amounts of phosphorylated protein as compared to non-neoplastic cells of the same cell type.

In view of the methods of identifying and prognosing patients for the likelihood of responsiveness to a particular cell-killing agent, the present invention provides another method of treating a patient for a neoplasia. The method comprises determining the activity state of the Syk and/or SHP-1 protein in a target neoplastic cell, and providing a treatment regimen based on the activity state that is determined. Where it is found that the levels of activity of all three of these proteins is within a normal range (as compared to non-neoplastic cells of the same type or another benchmark standard), a treatment regimen using the cell-killing agent of choice, alone, is implemented. Where it is found that the level of activity of one or more of these proteins is below the normal range (as compared to non-neoplastic cells of the same type or another benchmark standard), a treatment regimen using the cell-killing agent of choice and a substance that increases the amount of active Syk and/or SHP-1 (whichever was found to be deficient) is implemented. Administration of the agent and, optionally, substance can be accomplished in accordance with the teachings above.

In another aspect, the invention provides compositions. The compositions can comprise at least one substance that increases the amount of active Syk protein in a cell, at least one substance that increases the amount of active SHP-1 protein in a cell, or any combination of such substances. The compositions can also comprise at least one neoplastic cell-killing agent, such as an antibody that specifically targets CD33. The compositions can further comprise pharmaceutically acceptable carriers, binders, and the like, or biologically safe substances, such as salts, aqueous solvents, and the like.

The compositions of the invention generally comprise the biologically active components in combination with one or more other biologically active agent or a biologically inactive agent. The other biologically active agents can be any of a number of agents known to be suitable for inclusion in compositions to be exposed to in vitro or in vivo cells. For example, biologically active agents include, but are not limited to, antibiotics, growth factors, and anti-neoplastic agents. The biologically inactive agents include, but are not limited to, water or aqueous solutions, salts, buffers, fillers (e.g., for pharmaceutical compositions), binders, and the like.

In general, compositions of the invention that comprise a substance that increases active Syk and/or SHP-1 levels in a cell comprise sufficient amounts of the substance to increase the amount of active forms of these proteins in at least one cell to a level where the cell is more susceptible to a cell-killing agent. The increase can be any amount of increase that is detectable, including where detection is by cell death. Likewise, compositions of the invention that comprise a cell-killing agent comprise sufficient amounts of the agent to kill at least one cancer cell. Because the effect of the substance that increases the level of active Syk and/or SHP-1 in a cell increases the efficacy of cell-killing substances, the amount of cell-killing substance in a composition of the present invention may be less than the amount needed to achieve the same effect when administered according to other methods (e.g., when administered alone).

The compositions of the invention can be of any state of matter (i.e., solid, liquid, gas), but are typically solids, such as dried powders suitable for hydration with an appropriate solvent. Liquid compositions are envisioned as part of the invention; however, it is preferred that the liquid compositions be used in accordance with a method of the invention within a relatively short period of time after production, to ensure adequate activity of the substance(s) and agent(s) in the composition. Liquid compositions that are intended for long-term storage preferably contain one or more stabilizers or preservatives to enhance the shelf-life and activity of the active ingredients. Preferably, the compositions are sterile or capable of being sterilized by at least one common sterilization technique, such as heat (dry or wet), irradiation (UV, gamma, etc.), or filtration.

In yet another aspect, the invention provides at least one container that contains the substance that is capable of increasing the amount of active Syk and/or SHP-1 in a cell. The invention also provides at least one container that contains a substance that initiates a biological response resulting in death of a cell (i.e., a cell-killing agent). Thus, the invention provides containers that contain compositions of the invention. In embodiments, two or more containers are combined in a kit.

The container can be any container suitable for containing the compositions of the invention. Examples of suitable containers include, but are not limited to, glass, plastic, or metal, vials, ampules, tubes, or bottles. The containers can be sealed by any suitable type of seal, including, but not limited to, stoppers, screw caps, heat seals, and metal crimp seals. In general, the containers are of sufficient size (i.e., volume) to contain a composition of the invention. They typically are of sufficient size to accommodate additional components, such as water or another solvent.

In yet another aspect of the invention, one or more composition of the invention can be provided in a kit. In embodiments, one or more composition of the invention is provided in the kit, preferably in one or more containers. The kit is typically fabricated from paper products (e.g., cardboard), plastic, or metal, although it may be fabricated from any suitable material. The kit generally supplies some or all of the substances, compositions, and/or supplies and reagents necessary to practice a method of the invention. Thus, in embodiments, the kit comprises sufficient components to increase the amount of active Syk and/or SHP-1 protein in a cell cultured in vitro (e.g., in tissue culture). It may also contain sufficient components to screen candidate anti-neoplastic agents in vitro. Alternatively, in embodiments, the kit comprises sufficient components to increase the amount of active Syk and/or SHP-1 protein in a cancer cell found in vivo (e.g., in a subject suffering from cancer). It may also contain sufficient components to treat a subject suffering from cancer, by providing at least one substance that increases the level of active Syk and/or SHP-1 in a cancer cell and at least one cancer cell-killing agent. The kit of the invention can also contain ancillary supplies for delivering the substances or compositions of the invention to cells in vitro or in vivo. For example, it can contain syringes, needles, tubing, sterile water or water-based solvents for hydrating the substances or compositions.

EXAMPLES

The invention will be further explained by the following Examples, which are intended to be purely exemplary of the invention, and should not be considered as limiting the invention in any way.

The following Examples confirm that CD33 is a down-regulator of cell growth, mediating growth arrest and apoptosis, and that these effects are mediated by the protein tyrosine kinases Syk (or ZAP-70). The differential response of AML cells to CD33 ligation was associated with Syk/ZAP-70 expression. Understanding the mechanism(s) underlying CD33-induced inhibition of AML cells growth allowed us to focus on approaches that could enhance the inhibitory activity of the CD33 molecule. Ligation of CD33 directly activated an anti-proliferative pathway in myeloid leukemia cells, and increased apoptosis. These effects were mediated by the protein tyrosine kinase Syk, the protein phosphatase SHP-1, or combinations of both.

The examples are based on the following observations and provide solid bases for drawing the following conclusions:
   Anti-CD33 mAb directly inhibits proliferation of primary AML cells
   This activity depends on the intracellular level of the protein kinase Syk
   Syk is expressed in 70% of primary AML cells
   The response of AML cells to anti-CD33 mAb, including the immunotoxin gemtuzimab ozogamycin (GO; Mylotarg®, Wyeth), also depends on Syk activity
   5-azacytidine restores the response to anti-CD33 mAb (including GO) of Syk and SHP-1-negative cells
   Anti-CD33 mAb also induce phosphorylation of SHP-1

Example 1

Inhibitory Effect of Anti-CD33 Antibodies

AML cells express the cell surface antigen CD33 that serves as a down-regulator of cell growth. An anti-CD33 monoclonal antibody (mAb) coupled to a toxin (calicheamicin) is a licensed drug (gemtuzumab ozogamicin; GO; Mylotarg®, Wyeth) for the treatment of relapsed AML. Syk is not only an essential element in several cascades coupling antigen receptors to cell responses, but also Syk is a tumor suppressor gene. Silencing of Syk results in absence of Syk expression and unresponsiveness of tumor cells. It has been demonstrated that about 30% of the AML samples were Syk-negative and the response of leukemia cells to CD33 ligation correlated with Syk expression. Therefore, here we investigated whether or not the response of the AML cells to GO treatment also depends on the level of Syk expression. It is even more intriguing since 50% of Mylotarg is not conjugated to calicheamicin, and hence some of its activity is in fact due to anti-CD33 mAb signalling.

This example discloses data supporting the finding that the CD33 receptor on the surface of myeloid leukemia cells can function as a down-regulator of cell growth. It was previously shown that anti-CD33 mAb mediated growth arrest in a dose-dependent manner at a minimal concentration of 0.01 ug/ml. Importantly, we have now found that, while the optimal concentration of anti-CD33 mAb induced inhibition of proliferation up to 40% (FIG. 1B), in colony formation assays it was up to 60% (FIG. 1A). More specifically, FIG. 1A depicts the results of colony forming assays on HL-60 cancer cells. Approximately 200,000 cells were grown in 200 ul of culture media in the presence of media alone, media plus an anti-CD13 antibody, or media plus an anti-CD33 antibody.

More specifically, for Panel A, colony formation assays were performed as follows: HL-60 cells were treated and cultured in 0.3% agarose in triplicate for each condition in the presence of 0.01 ug/ml of antibodies. After 14 days of culture, the number of colonies was enumerated in each dish. The basal level of colony formation (>400 per dish) was considered as 100% and the percentage of stimulation was calculated for each condition. Error bars in the figure indicate the SEM. Each graph is representative of at least 3 independent experiments. For Panel B, primary leukemia cells were cultured for 48 hours in the presence of 0.01 ug/ml of anti-CD33 mAb or control mouse IgG. Each bar in the figure summarizes (median) the proliferative response of that group. The basal level of untreated cell proliferation (CPM>5500 CPM) was considered as 0%. Inhibition was calculated as the percent change for that condition. Error bars indicate the SEM. Bars marked with asterisk have mean values that are significantly higher than that of the control condition (p<0.02, Student's t-test).

The results of the experiment show that anti-CD33 antibody, but not media alone or media plus anti-CD13 antibody, inhibited colony formation, and thus cell growth. The inhibition was significant.

Earlier findings indicated that, upon CD33 ligation, Syk, in contrast to the src-family kinases (fyn, lyn), became phosphorylated and engaged in CD33 downstream signaling. Based on these observations, we tested a panel of 25 primary AML samples for Syk expression using standard Western blotting and an anti-Syk or anti-ZAP-70 mouse monoclonal antibody from Santa Cruz Biochem.

About 30% of primary AML cells demonstrated undetectable Syk by Western blot. Meanwhile, we noted that the differential response of AML cells to CD33 ligation induced inhibition was associated with the level of Syk (or, in two cases, ZAP-70) expression. Based on Syk expression in primary AML cells and their response to CD33 ligation we distinguished 4 groups of AML samples (see FIG. 1B): Syk+ responders; Syk+ non-responders; Syk−/ZAP-70+ responders; and Syk− non-responders. In cells that were Syk− but ZAP-70 positive, it appears that ZAP-70 provides the function of the Syk protein, within the context of the invention.

In the Syk-positive (or ZAP-70-positive) groups the number of Responsive samples was significantly higher as compared to the Syk-negative/ZAP-70-negative groups (FIG. 1C), suggesting a correlation between Syk expression and responsiveness of AML cells to CD33 ligation (p<0.02).

Example 2

Elucidation of CD33 Signalling Pathway Members

To further understand the mechanism of action of anti-CD33 antibody on neoplastic cells, we treated leukemia cells with anti-CD33 antibody or anti-CD13 antibody, and determined the effect on certain proteins. More specifically, primary AML cells at about 1 million cells in 1 ml of media, which were either Syk+ responder or Syk+ non-responder cells were treated for 20 minutes with 10 ug/ml of anti-CD33 mAb 251 (Medarex, Princeton, N.J.) or isotype-matching control anti-CD13 mAb (monoclonal IgG1; Cell Science Inc, Norwood, Mass.) at room temperature. The cells were then treated by addition of 20 ug/ml of polyclonal rabbit anti-mouse IgG for 2 minutes at 37° C. The treatment was performed in the presence of 10% human AB serum. Cell lysates were prepared using standard techniques and they were used to generate immune precipitates with appropriate mAb.

Figure 2:
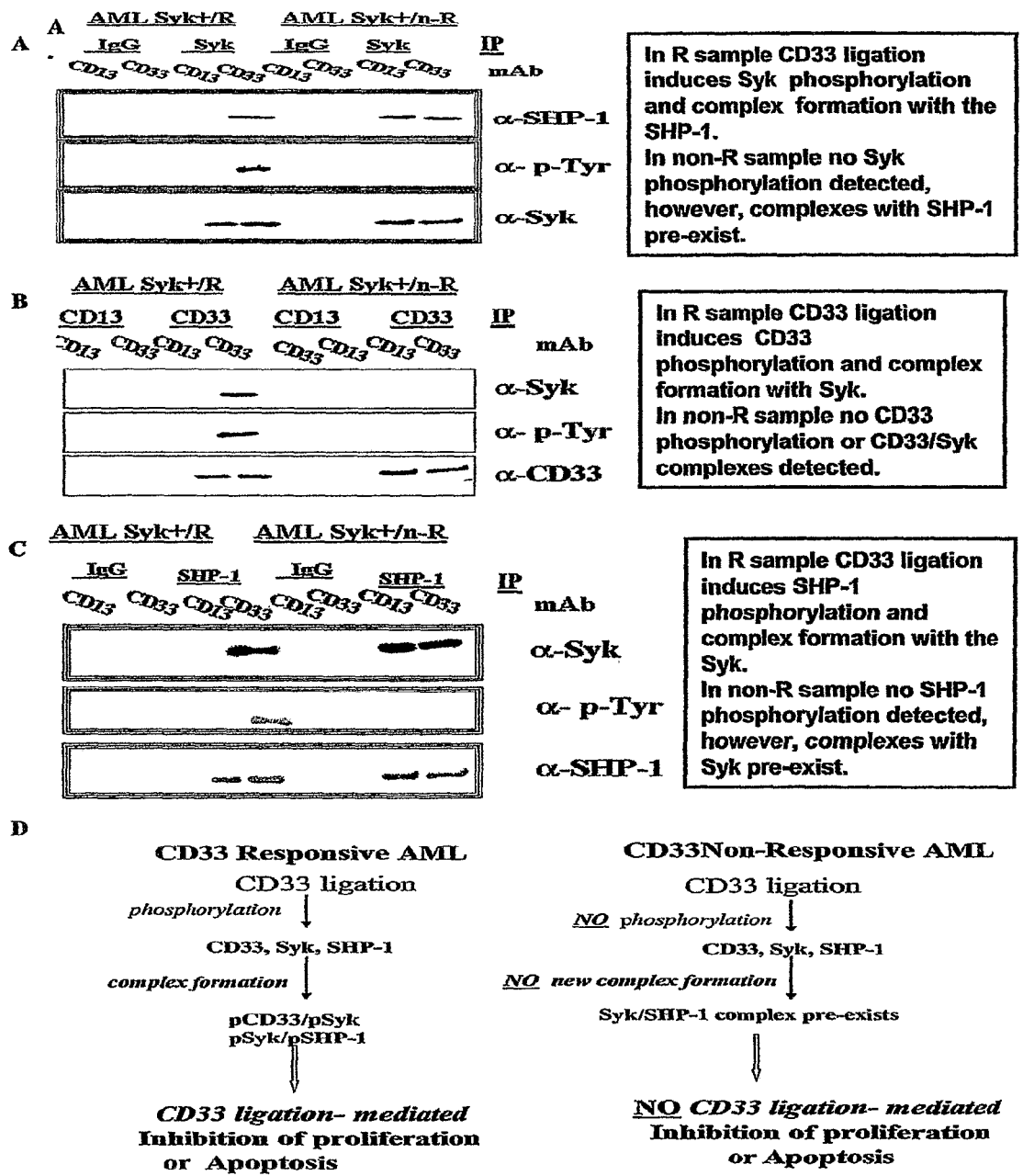
FIG. 2 shows the involvement of Syk and SHP-1 in CD33-mediated cell killing cascade. Panel A shows immunoprecipitation (IP) assays for Syk and SHP-1 in anti-CD33 treatment responders and non-responders. Panel B shows IP assays for Syk and CD33 in anti-CD33 treatment responders and non-responders. Panel C shows IP assays for Syk and SHP-1 in anti-CD33 treatment responders and non-responders. Panel D shows the intracellular effects of CD33 ligation in responders and non-responders.

The results presented in FIG. 2 show that binding of an anti-CD33 antibody to a CD33 receptor on the cell surface initiates a signalling pathway that results in phosphorylation and activation of Syk in responder cells, but not in non-responder cells (see FIG. 2A). The results also show that, in responder cells, binding of an anti-CD33 antibody to a CD33 receptor results in formation of complexes containing active Syk and active SHP-1 (see FIG. 2A). This result implicates active Syk as a required member of the signalling pathway that leads to cell death as a result of binding of an anti-CD33 antibody to the cell.

In addition, the results presented in FIG. 2B show that binding of an anti-CD33 antibody to a CD33 receptor on the cell surface results in CD33 phosphorylation and complex formation with Syk. The results also show that, in non-responder cells, no CD33 phosphorylation occurs and no complexes involving CD33 and Syk are formed. These results further implicate active Syk as a required member of the signalling pathway that leads to cell death as a result of binding of an anti-CD33 antibody to a cell.

FIG. 2C shows that the protein phosphatase SHP-1 is also involved in signal transduction from CD33. More specifically, the results presented in FIG. 2C show that, in responder cells, binding of an anti-CD33 antibody to the CD33 molecule induces SHP-1 phosphorylation (activation). It also results in formation of complexes between active Syk and active SHP-1. In contrast, ligation of the CD33 by anti-CD33 antibody does not result in phosphorylation of SHP-1. These results implicate active SHP-1 as a member of the signal transduction pathway from CD33 to cell death.

FIG. 2D summarizes the results of FIGS. 2A-C. More specifically, FIG. 2D depicts two distinct sets of events that occur in responder and non-responder cells. In responder cells, ligation of CD33 results in phosphorylation of CD33, Syk, and SHP-1, complex formation between CD33, Syk, and SHP-1, and signal transduction from the cell surface molecule to the nucleus, where global effects are seen, such as inhibition of cell proliferation and cell death, primarily through an apoptotic pathway. In contrast, in non-responder cells, no phosphorylation of CD33, Syk, or SHP-1 occurs, no new complexes involving Syk, SHP-1, and/or CD33 are made, no inhibition of proliferation or growth is seen, and no cell death is observed. Similar results were obtained for CD33-responsive ZAP-70-positive AML samples, showing that, in some cells, ZAP-70 can substitute for Syk.

Example 3

Proliferative Response of Primary AML Cells to Mylotarg® (Wyeth) and Correlation with Syk Activity With the knowledge of the effect of a naked anti-CD33 antibody on Syk activation and cell proliferation or death, we investigated the effect of an immunotoxin (GO; Mylotarg® (Wyeth)) on these characteristics. GO was selected based on its approval status by the FDA. Proliferation assays were performed as described above. Various concentration of GO were added at the initiation of 48 hour culture. The basal levels of cell proliferation (untreated cells) were >10000 cpm and were considered as 100%. The percentage of change was calculated for each condition for each sample. Summarized data (median) for 25 Syk-positive and 15 Syk-negative samples are presented in FIG. 6. Error bars indicate the SEM.

Because we had shown that the response of AML cells to CD33 ligation correlates with Syk expression, we investigated whether their response to GO would also depend on the presence of Syk. It is widely held that 50% of the antibody portion of the Mylotarg® (Wyeth) product is not conjugated to calicheamicin, raising the intriguing hypothesis that some of this product's activity is, in fact, due to signaling induced by the binding to CD33, rather than delivery of the toxin to the cell. We designed experiments to investigate the role of each portion of the product, and to further understand the biochemical events resulting from CD33 ligation in responder and non-responder cells.

Figure 3:
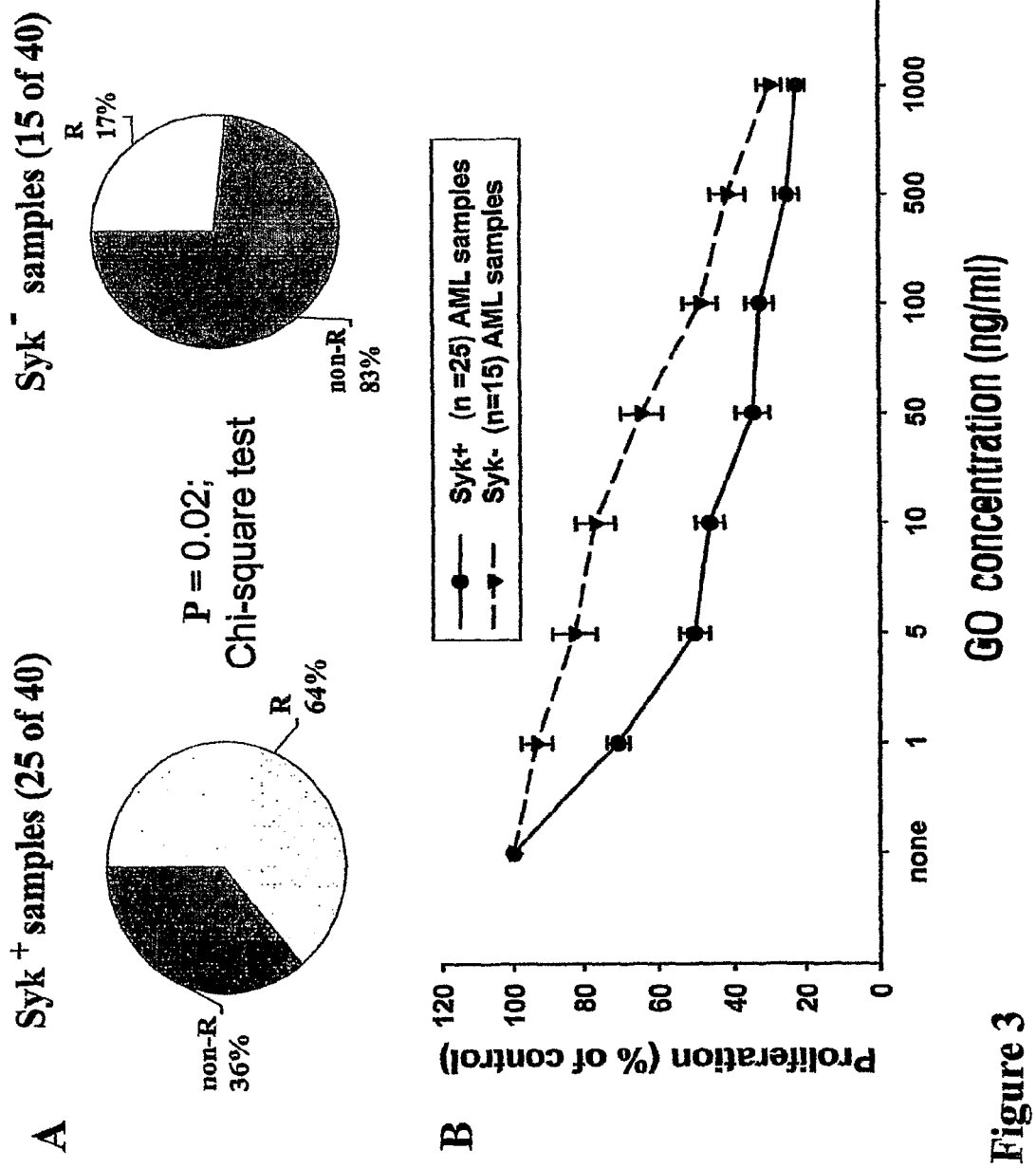
FIG. 3 shows the proliferative response of primary AML samples to Mylotarg® (Wyeth). Panel A shows a pie chart depicting the correlation of responders to active Syk presence. Panel B shows a proliferation assay and the effect of Mylotarg® (Wyeth) on proliferation as a function of Syk presence.

As shown in FIG. 3A, in Syk-positive samples, the number of responsive samples was significantly higher (83%) than the number of responsive samples in Syk-negative samples (17%). Moreover, as shown in FIG. 3B, analysis of the proliferative response of primary AML samples to GO revealed that in both Syk-positive and Syk-negative samples, GO induced dose-dependent inhibition. However, in Syk-positive samples, the level of inhibition was significantly ($p<0.003$, Student's t-test) higher than in Syk-negative samples. That difference was more prominent at low doses of GO and diminished at higher doses, probably due to toxin activity. Together these data suggest a correlation between the response of primary AML cells and the inhibitory activity of GO. They further show a correlation between the response of primary AML cells and the presence of Syk. Finally, they further suggest that, at least at low doses of GO, the presence of Syk enhances the activity of GO.

Example 4

Effect of Blocking Syk Activity on the Effectiveness of Anti-CD33 Antibody Treatment of Cells To test whether there is a correlation between response of AML cells to CD33 ligation and/or GO treatment and the level of their Syk expression, "blocking" experiments were performed. In order to block Syk expression, we used Syk-si-RNA transfection. More specifically, for the results presented in FIGS. 4A and 4B, HL-60 cells were transfected with Syk si-RNA or control RNA and grown in cell culture under normal conditions for these cells. 72 hours post-transfection, cells were cultured in the presence of optimal (0.1 mg/ml) concentration of mAb, as disclosed above (FIG. 4A) or the indicated concentrations of Mylotarg® (Wyeth) (FIG. 4B). Proliferation assays were performed as described above. The basal level of proliferation was >10000 CPM (considered as 100%). Each point represents the percent change for that condition. Error bars indicate the SEM. Bars compared and marked with asterisk have a statistically significant difference. For FIG. 4C, HL-60 cells were transfected with Syk si-RNA or control RNA. After 72 hours of culture under typical culture conditions, cell lysates were prepared and used to generate immune precipitates with the appropriate mAb.

Figure 4:
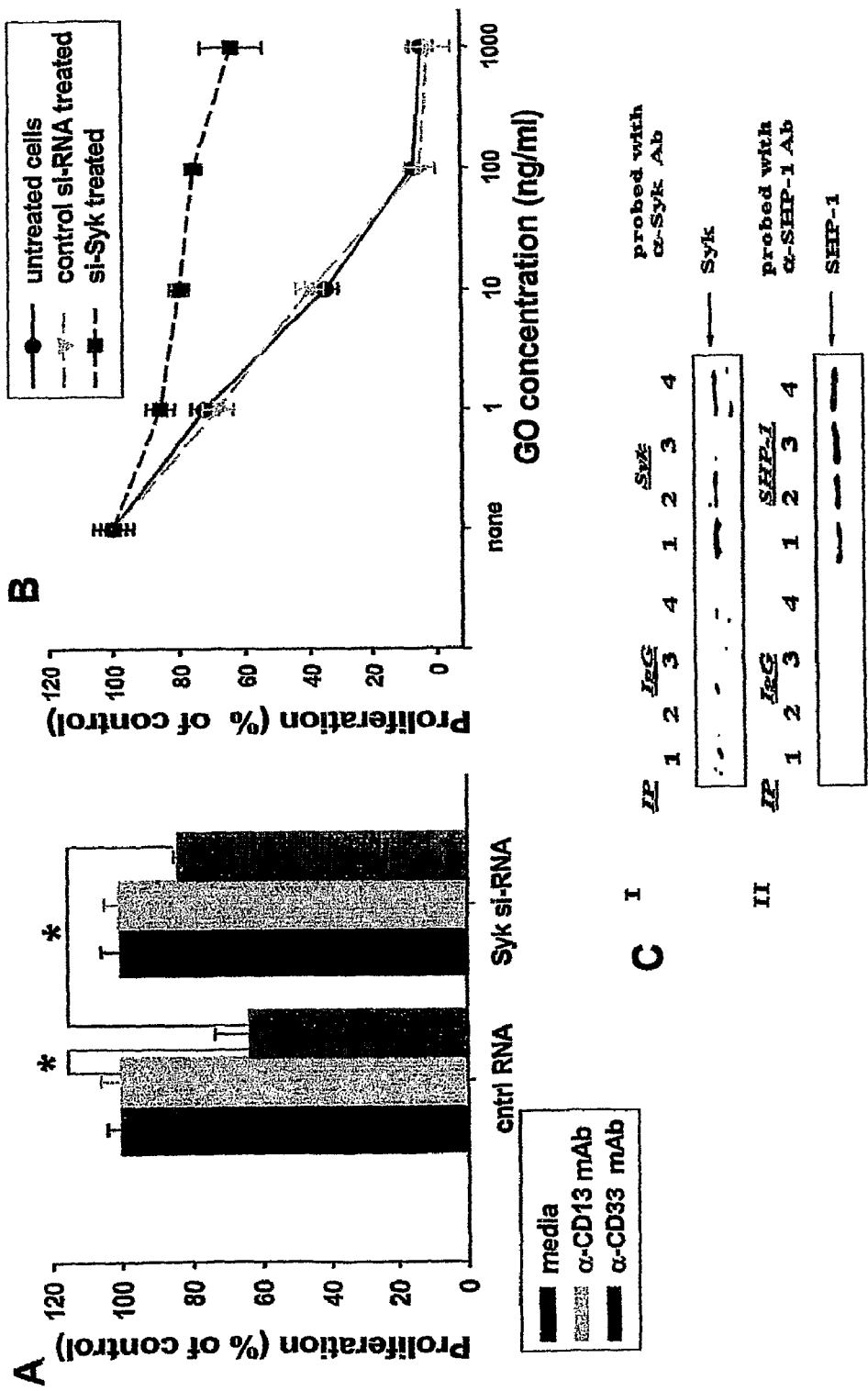
FIG. 4 shows the effect of blocking Syk activity on anti-CD33 effectiveness. Panel A shows a bar graph of a proliferation assay performed in the presence or absence of anti-CD33 antibody and Syk. Panel B shows a proliferation assay using Mylotarg® (Wyeth) on cells treated with siRNA specific for Syk. Panel C shows IP assays of cells treated with Syk siRNA.

As is shown in FIG. 4, blocking the function of protein kinase Syk resulted in conversion of responder cells to non-responsiveness. That is, the significant drop in proliferation seen in cells treated with control RNA and anti-CD33 antibody is abolished in cells that are treated with Syk siRNA and anti-CD33 antibody. Indeed, the difference between cells treated with anti-CD33 antibody and those treated with anti-CD13 antibody is insignificant in the presence of Syk siRNA, whereas there is a significant difference between the amount of proliferation seen in anti-CD33 antibody treated cells in the presence or absence of Syk siRNA. Moreover, Syk si-RNA-transfected cells demonstrated a significantly lower response to Mylotarg® (Wyeth) treatment than control RNA treated or untreated cells (FIG. 4B). Furthermore, 72 hours post-transfection, Syk was undetectable by Western blot, while the level of SHP-1 was un-changed (FIG. 4C).

Example 5

Further Investigations on the Role of SHP-1

In order to further test the involvement of SHP-1 in responsiveness to various treatments, we performed "blocking" experiments by down-regulating the level of SHP-1 protein with SHP-1 si-RNA. The results are presented in FIG. 5. Panel A shows a proliferation assay, which was performed as described above. The basal level of untreated cell proliferation (CPM>12000 CPM) was considered as 100%. Percent change was calculated for each condition. Error bars indicate the SEM. Bars compared and marked with asterisks have a statistically significant difference. Panel B shows Western blot data.

Figure 5:
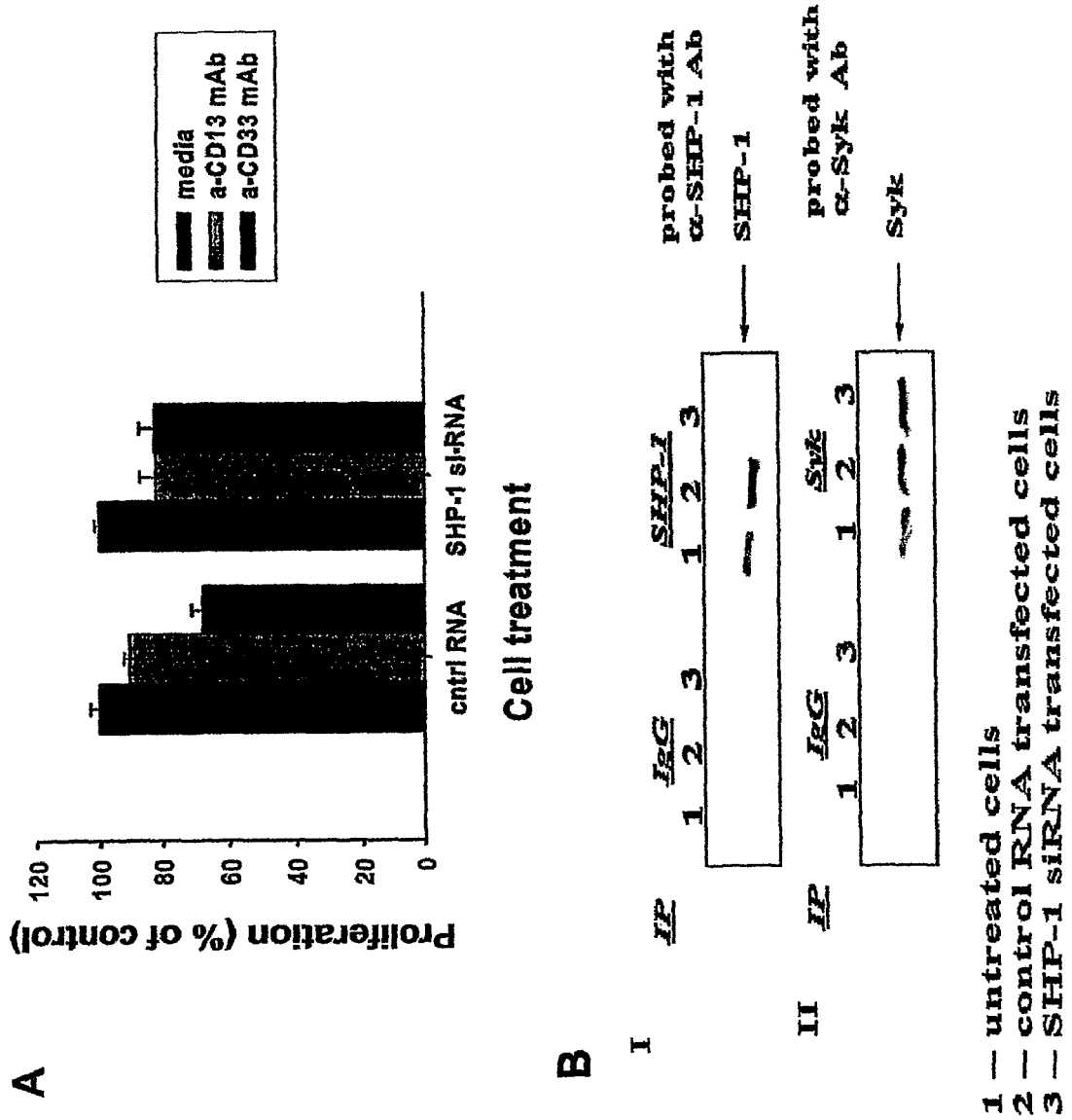
FIG. 5 shows bar graphs and Co-IP assays of the effect of SHP-1 siRNA treatments on proliferation of cells and on complex formation between SHP-1 and Syk.

HL-60 cells were transfected with SHP-1 si-RNA or control RNA. 24 hours after transfection, SHP-1 expression in SHP-1 si-RNA treated cells (in contrast to controls) was undetectable by Western blot (see FIG. 5B), while the expression of Syk was unchanged. Proliferation assays revealed that addition of anti-CD33 mAb did not induce inhibition of proliferation in SHP-1 si-RNA transfected cells, while in control RNA transfected cells the level of inhibition (up to 30%) was similar to untreated cells (FIG. 5, Panel A).

Figure 6:
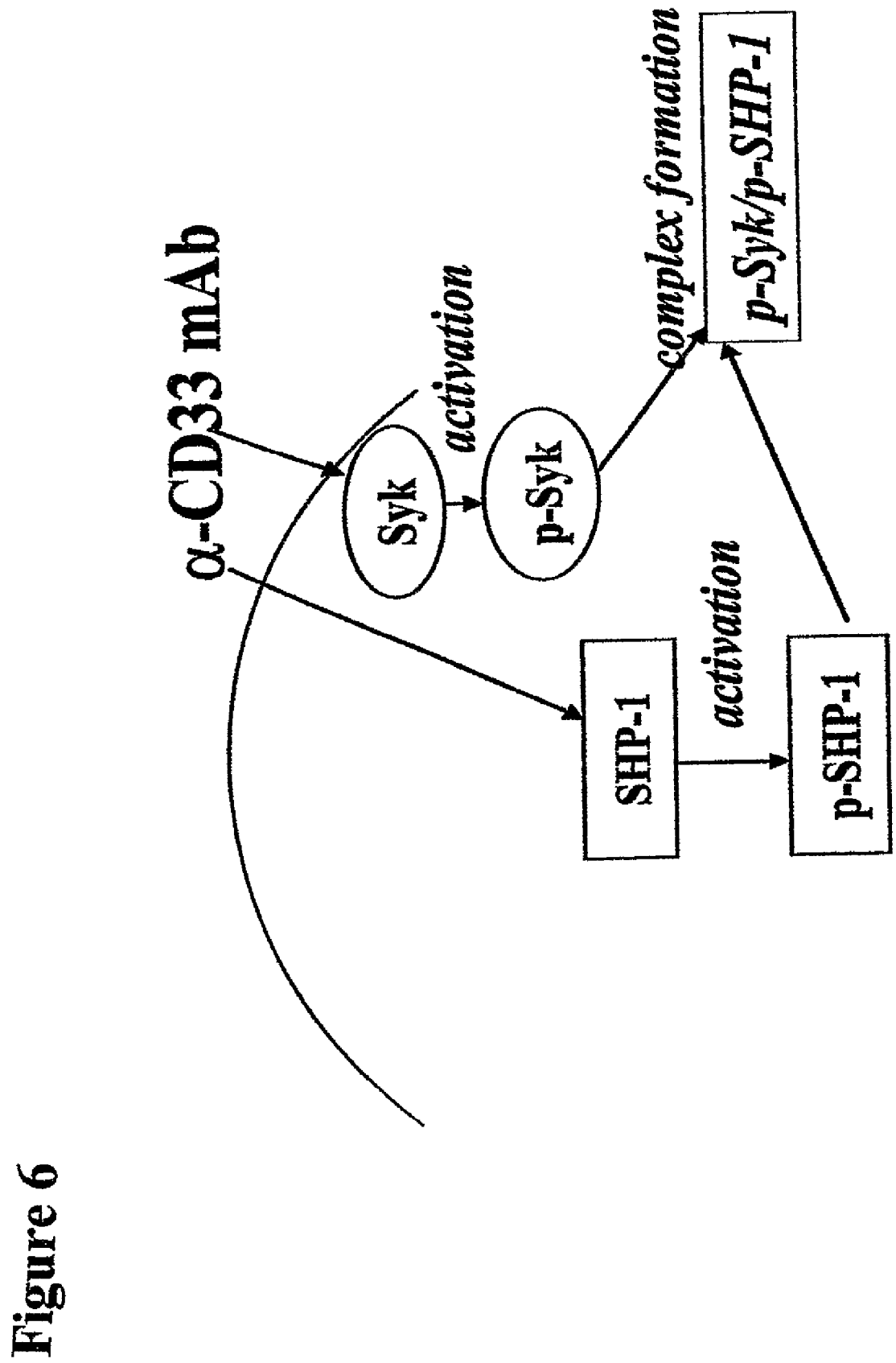
FIG. 6 shows a signalling pathway connecting Syk and SHP-1 activation and anti-CD33 treatments.

Based on these results, a model for activation of CD33 and a signal transduction pathway is depicted in FIG. 6. As can be seen in FIG. 6, the present invention provides not only for improved treatments of neoplastic cells, and in particular cells that have proven to be non-responsive to antibody therapy, but also provides a biochemical basis for those treatments. The invention identifies SHP-1 as a common participant in signal transduction and chemotherapy responsiveness, and identifies it as a target, along with Syk, for development of new drugs, or for re-screening of known drugs, for effective treatment of neoplasias.

Example 6

Effect of 5-Azacytidine on Cells

To evaluate the effect of certain chemotherapeutic agents on signal transduction through Syk and/or SHP-1, experiments were performed on primary AML samples. Primary leukemia cells were treated with 5-azacytidine for 4 days under otherwise normal cell culture growth conditions. The cells were then washed twice, and a proliferation assay was performed as described above. The basal level of proliferation (untreated cells) was considered as 100% and the percent change was calculated for each condition. Error bars indicate the SEM.

Syk is not only an important protein kinase, but also a tumor suppressor. In many cancer cells, Syk is silenced by hypemethylation of the DNA encoding it. This hypermethylation can lead to absence of Syk expression and, as a result, to unresponsiveness of tumor cells to various treatments. To block possible hyper-methylation and restore Syk expression in Syk-negative primary AML samples, we used 5-azacytidine. Other hypomethylating agents could work as well. The results of the experiments are depicted in FIG. 7, Panels A-D.

Figure 7:
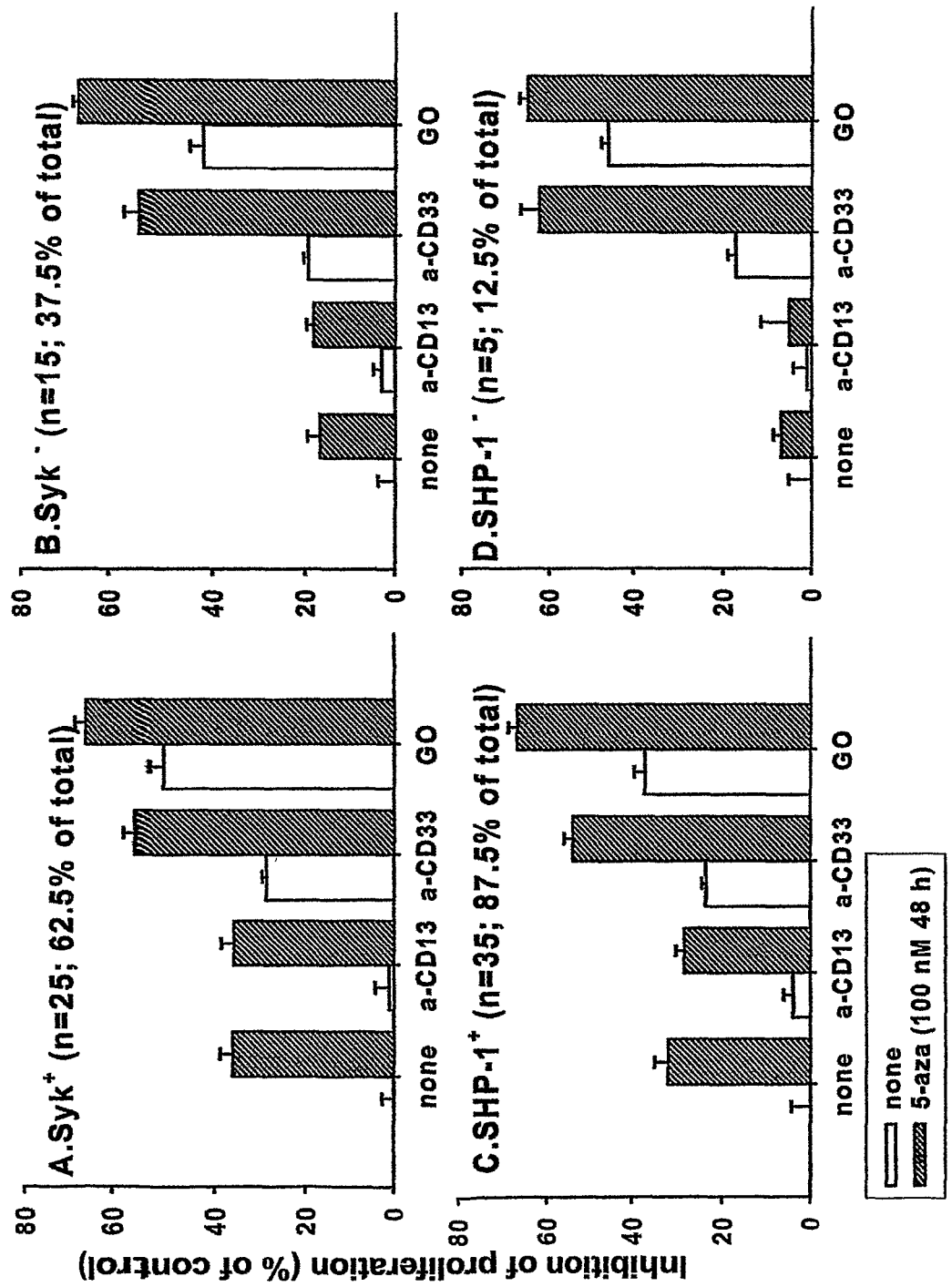
FIG. 7 depicts bar graphs of the effect on proliferation of 5-azacytidine and GO on Syk+ and Syk− cells.

As can be seen in FIG. 7, Panel A, Syk+ cells that are untreated or treated only with an anti-CD13 antibody show the same (normal) level of inhibition of proliferation in the assay. In contrast, Syk+ cells that are treated with both an anti-CD33 antibody (naked antibody or GO) and 5-azacytidine show increased inhibition of proliferation. This result indicates that hypomethylation of Syk+ cells enhances the inhibitory effect of anti-CD33 antibody treatment.

As can be seen in FIG. 7, Panel B, Syk– cells treated in a similar fashion as the Syk+ cells in Panel A show essentially the same pattern of response to the treatments. In 15 Syk-negative primary AML samples, 5 (33%) showed restored Syk expression after 5-azacytidine treatment, while in the Syk-positive samples the level of Syk expression was unchanged (data not shown). This result is especially interesting because it shows that the low level of effect of anti-CD33 antibodies on Syk– cells (non-responders) can be substantially increased by treatment of the cells with a hypomethylating agent. Thus, non-responder cells can be converted to responder cells by treating with a hypomethylating agent.

Moreover, in 2 of 5 (40%) SHP-1-negative primary AML samples, 5-azacytidine treatment also restored SHP-1, thus indicating not only that hypermethylation results in down-regulation of SHP-1, but also indicating that active SHP-1 is involved in signal transduction from CD33 ligation to cell proliferation inhibition and cell death. It further indicates that hypomethylating agents can reverse the effects of hypermethylation on SHP-1 expression, and render non-responder cells responsive to anti-CD33 treatments.

In sum, these proliferation assays revealed that the responses of primary AML cells to 5-aza alone depends on the levels of Syk or SHP-1 expression. In Syk-positive or SHP-positive samples, the level of 5-aza-mediated inhibition of proliferation is significantly higher. However, combined treatment of Syk-negative or SHP-1-negative samples with 5-aza and anti-CD33 mAb or Mylotarg® (Wyeth) resulted in a level of inhibition comparable to positive samples.

It will be apparent to those skilled in the art that various modifications and variations can be made in the practice of the present invention without departing being from the scope or spirit of the invention. Other embodiments of the invention will be apparent to those skilled in the art from consideration of the specification and practice of the invention. It is intended that the specification, including the examples, be considered as exemplary only, with a true scope and spirit of the invention being indicated by the following claims.

The invention claimed is:

1. A method of increasing the efficacy of a cell-killing agent on a neoplastic cell that expresses CD33, said method comprising:
   exposing the neoplastic cell to a substance that increases the amount of functional Syk protein kinase, SHP-1 protein phosphatase, or both, in the neoplastic cell,
   determining the presence or activity level of said Syk protein, SHP-1 protein, or both in said neoplastic cell in response to the exposure, wherein the presence or level of active Syk protein, SHP-1 protein, or both is indicative of a likelihood of successful treatment of a neoplasia with said cell-killing agent, and
   recommending administering a therapeutically effective amount of said cell-killing agent based upon the determination of the presence or activity of said Syk protein, SHP-1 protein, or both in said neoplastic cell, thereby increasing the efficacy of the cell-killing agent on the neoplastic cell.

2. The method of claim 1, wherein the method increases the amount of functional Syk in the cell.

3. The method of claim 1, wherein the method increases the amount of functional SHP-1 in the cell.

4. The method of claim 1, further comprising exposing the cell to the cell-killing agent.

5. The method of claim 1, wherein the substance is a hypomethylating or demethylating substance.

6. The method of claim 5, wherein the substance is 5-Azacytidine (azacytidine; 5-Aza-CR), 5-Aza-2'-deoxycytadine (decitabine; DAC; 5-Aza-CdR), 5,6-dihydro-5-azacytidine, procaine, procainamide, (–)-egallocatechin-3-gallate (EGCG), or Zebularine.

7. The method of claim 1, wherein the cell-killing agent is a substance that is involved in a cascade of biological and biochemical activities that results in death of the cell, wherein the Syk protein kinase or the SHP-1 protein phosphatase is also involved in the cascade.

8. The method of claim 7, wherein the cell-killing agent is an antibody that binds to CD33 on the surface of the cell.

9. The method of claim 8, wherein the cell-killing agent is an anti-CD33 antibody, antibody fragment, immunotoxin, or immunoconjugate.

10. A method of treating a neoplasia, said method comprising:
    administering at least one substance that increases the amount of functional Syk protein kinase, SHP-1 protein phosphatase, or both, in at least one cell of the neoplasia,
    determining the presence or activity level of said Syk protein kinase, SHP-1 protein phosphatase, or both, in said neoplastic cell in response to administration of said substance to said cell; and
    providing information about the determination for clinical administration of a therapeutically effective amount of at least one cell-killing agent based upon the presence or activity of said Syk protein, SHP-1 protein, or both in said neoplastic cell.

11. The method of claim 10, wherein the substance is 5-azacytidine.

12. The method of claim 10, wherein the cell-killing agent is a substance that is involved in a cascade of biological and biochemical activities that results in death of the cell, wherein the Syk protein kinase, the SHP-1 protein phosphatase, or both, is also involved in the cascade.

13. The method of claim 12, wherein the cell-killing agent is an anti-CD33 antibody, antibody fragment, immunotoxin, or immunoconjugate.

14. The method of claim 10, further comprising administering the therapeutically effective amount of at least one cell-killing agent that targets CD33.

15. The method of claim 10, wherein the neoplasia is leukemia.

16. The method of claim 15, wherein the leukemia is acute myeloid leukemia (AML).

17. A method of treating a patient for a neoplasia characterized by cells that express CD33, said method comprising:
    obtaining the amount or activity state of the Syk protein kinase, SHP-1 protein phosphatase, or both, in at least one neoplastic cell of the neoplasia, and
    providing a treatment regimen based on the amount or activity state that is determined for clinical administration of a therapeutically effective amount of a cell-killing agent that targets CD33 based upon the amount or activity state of the Syk protein kinase, SHP-1 protein phosphatase, or both, in said neoplastic cell of the neoplasia.

18. The method of claim 17, comprising:
    determining that the levels of active Syk protein kinase, SHP-1 protein phosphatase, or both, are within normal ranges, and administering a cell-killing agent that targets CD33 on the neoplastic cell of interest.

19. The method of claim 18, wherein the cell-killing agent is an antibody.

20. The method of claim 17, comprising:
    determining that the levels of active Syk protein kinase, SHP-1 protein phosphatase, or both, are below the normal range,
    administering a therapeutically effective amount of a substance that increases the level of active Syk protein kinase, SHP-1 protein phosphatase, or both, said substance being selected based on the particular protein that is present in an insufficient amount, and
    administering a therapeutically effective amount of a cell-killing agent that targets CD33 on the neoplastic cell of interest.

21. The method of claim 20, wherein the cell-killing agent is an antibody that binds to CD33.

* * * * *